(12) United States Patent
Bailey, Jr. et al.

(10) Patent No.: US 7,947,827 B2
(45) Date of Patent: May 24, 2011

(54) PHARMACEUTICAL FORMULATION COMPRISING A METALOPORPHYRIN AND METHOD FOR ITS PURIFICATION AND USE

(75) Inventors: George S. Bailey, Jr., Corvallis, OR (US); Carole Jubert, Corvallis, OR (US)

(73) Assignee: State of Oregon Acting By and Through The State Board of Higher Education on Behalf of Oregon State University, Corvallis, OR (US)

( * ) Notice: Subject to any disclaimer, the term of this patent is extended or adjusted under 35 U.S.C. 154(b) by 489 days.

(21) Appl. No.: 11/825,146

(22) Filed: Jul. 2, 2007

(65) Prior Publication Data

US 2008/0139524 A1 Jun. 12, 2008

Related U.S. Application Data

(60) Provisional application No. 60/817,978, filed on Jun. 30, 2006, provisional application No. 60/923,842, filed on Apr. 16, 2007.

(51) Int. Cl.
*C07B 47/00* (2006.01)
*C07D 487/22* (2006.01)

(52) U.S. Cl. ........................................................ 540/145

(58) Field of Classification Search .................. None
See application file for complete search history.

(56) References Cited

U.S. PATENT DOCUMENTS

| | | | |
|---|---|---|---|
| 4,649,043 A | 3/1987 | Urquhart et al. | |
| 5,650,292 A | 7/1997 | Scherz et al. | |
| 5,770,404 A | 6/1998 | Camiener | |
| 6,777,402 B2 | 8/2004 | Nifantiev et al. | |
| 2003/0088092 A1 | 5/2003 | Nifantiev | |

FOREIGN PATENT DOCUMENTS

WO WO 2005/089713 9/2005

OTHER PUBLICATIONS

Bidigare et al. Analytical Chemistry, 1991, 63, 130-133.*
Aman et al. Journal of Chromatography A, 2005, 1074, 99-105.*
Chronakis et al. Colloids & Surfaces A: Physicochemical & Engineering Aspects, 2000, 173, 181-192.*
"Aliphatic compounds", IUPAC Compendium of Chemical Terminology, 1997, 67, p. 1313.*
Choe et al. Journal of Food Science, 2001, 66(8), 1074-1079.*
Kost. Handbook of Chromatography, 1988, Editors Gunter Zweig and Joseph Sherma, pp. 261-265.*
Abraham et al., "Role of chlorophyllin as an in vivo anticlastogen: protection against gamma-radiation and chemical clastogens," *Mutat Res* 322:209-212 (1994).
Albertsson & Svensson, "Counter-current distribution of sonicated inside-out thylakoid vesicles," *Mol. Cell Biochem.* 81(2):155-63, 1988.
Arimoto et al., "Binding of polycyclic planar mutagens to chlorophyllin resulting in inhibition of the mutagenic activity," *Mutat Res* 287:293-305 (1993).

Bailey et al., "Quantitative carcinogenesis and dosimetry in rainbow trout for aflatoxin $B_1$ and aflatoxicol, two aflatoxins that form the same DNA adduct," *Mutat Res* 313:25-38 (1994).
Botelho et al., "Chlorophyllin protects HEp-2 cells from nuclear fragmentation induced by poliovirus," *Lett Appl Microbiol* 39:174-177 (2004).
Brockmann, "Zur absoluten Konfiguration des Chlorophylls," *Angew. Chem.*, 80(6):233-234 (1968).
Carter et al., "The Dietary Phytochemical Chlorophyllin Alters E-Cadherin and β-Catenin Expression in Human Colon Cancer Cells," *The Journal of Nutrition*, 134:3441S-3444S (2004).
Dashwood & Guo, "Inhibition of 2-amino-3-methylimidazo[4,5-f]quinoline (IQ)-DNA binding by chlorophyllin: studies of enzyme inhibition and molecular complex formation," *Carcinogenesis* 13(7):1121-1126 (1992).
Dashwood, "The importance of using pure chemicals in (anti) mutagenicity studies: chlorophyllin as a case in point," *Mutat Res* 381:283-286 (1997).
Dashwood, R. & C. Liew: Chlorophyllin-enhanced excretion of urinary and fecal mutagens in rats given 2-amino-3-methylimidazo[4,5-f]quinoline. Environ Mol Mutagen 20:199-205, (1992).
Du, Q. et al., "Relationship between the flow-rate of the mobile phase and retention of the stationary phase in counter-current chromatography," *Journal of Chromatography, A* 835:231-235 (1999).
Du, Q. et al., "Preparative separation of isoflavone components in soybeans using high-speed counter-current chromatography," *Journal of Chromatography, A* 923(1-2):271-274 (2001).
Espinosa-Aguirre et al., "Mutagenic activity of urban air samples and its modulation by chili extracts," *Mutat Res* 303:55-61 (1993).
Ghosh et al., "Comparative efficacy of chlorophyllin in reducing cytotoxicity of some heavy metals," *Biol Met* 4:158-161 (1991).
Gorelick, "Risk assessment for aflatoxin: I. Metabolism of aflatoxin $B_1$ by different species," *Risk Anal* 10(4):539-559 (1990).
Greenwald, "Diet and cancer. Perspectives of prevention," *Advances in Nutrition and Cancer* 472:1-19 (1999).
Gustafson & Martell, "A kinetic study of the Copper(II) Chelate-catalyzed hydrolysis of isopropyl methylphosphofluoridate (sarin)," *Journal of the American Chemical Society* 62:2309-2317 (1962).
Gustafson & Martell, "Formation of polynuclear complexes in aqueous solution," *Ann N Y Acad Sci* 88:322-331 (1960).

(Continued)

*Primary Examiner* — Noble Jarrell
(74) *Attorney, Agent, or Firm* — Klarquist Sparkman, LLP

(57) ABSTRACT

Pharmaceutical formulation for the prophylaxis, pretreatment and treatment of a poisoning caused by exposure to (either singly or as a mixture of agents) organophosphorus cholinesterase inhibitors, vesicating agents, polycyclic aromatic hydrocarbons, and aflatoxin B1. This invention is characterized by active substance comprised of a metaloporphyrin molecule with an associated metal moiety (Cu, Mg) of suitable purity and chemical composition to provide a bioavailable oral dosage form to attain predictable concentrations in target tissues and bodily fluids (plasma, bronchial secretions, etc.) sufficient to counteract the effects of toxic substances through chemical complexation or catalysis of toxin degradation. Although these metaloporphyrins are semisynthetic products of chlorophyll, the preferred starting material is chlorophyll a (Chla) extracted and purified from *Spirulina pacifica* or other sources. A specific method is invented to achieve a critical combination of purity and yield beyond those currently available.

13 Claims, 16 Drawing Sheets

OTHER PUBLICATIONS

Hainer, "Studies of copper chlorophyllin-odorant systems," *Science* 119:609-610 (1954).

Hammond & Forster, "A polymeric amine-copper(II) complex as catalyst for the hydrolysis of 1,2,2-trimethylpropyl methylphosphofluoridate (soman) and bis (1-methylethyl) phosphorofluoridate (DFP)," *Applied Polymer Science* 43:1925-1931, (1991).

Harrison et al., "The Safety and Fate of Potassium Sodium Copper Chlorophyllin and Other Copper Compounds," *J. Amer. Pharm. Assoc.* 43:722-737 (1954).

Harttig & Bailey, "Chemoprotection by natural chlorophylls in vivo: inhibition of dibenzo[a,1]pyrene-DNA adducts in rainbow trout liver," *Carcinogenesis* 19(7):1323-1326, (1998).

Hay & Govan, "The [Cu(tmen)(OH)(OH$_2$)]$^+$ promoted hydrolysis if 2,4-dinitrophenyl diethyl phosphate and O-isopropyl methylphosphonofluoridate (Sarin) (tmen=$N,N,N',N'$-tetramethyl-1-1,2-diaminoethane)," *Polyhedron* 17(11-12):2079-2085 (1998).

Hayashi et al., "Mechanisms of Chlorophyllin Anticarcinogenesis: Dose-Responsive Inhibition of Aflatoxin Uptake and Biodistribution Following Oral Co-administration in Rainbow Trout," *Toxicology and Applied Pharmacology* 158:132-140 (1999).

Imaizumi et al., "Metabolism and toxicity of acid phosphate esters, metabolites of organophosphorous insecticides, in rat," *Japanese Journal of Toxicology and Environmental Health* 39:566-571 (1993).

Ito, "Recent advances in counter-current chromatography," *Journal of Chromatography* 538(1):3-25, (1991).

Ito, "Golden rules and pitfalls in selecting optimum conditions for high-speed counter-current chromatography," *Journal of Chromatography, A* 1065(2):145-168, (2005).

Ito & Bowman, "Countercurrent chromatography: liquid-liquid partition chromatography without solid support," *Science*, 167(916):281-283, (1970).

Kensler et al., "Predictive value of molecular dosimetry: individual *versus* group effects of oltipraz on aflatoxin-albumin adducts and risk of liver cancer," *Cancer Epidemiol Biomarkers Prev* 6:603-610 (1997).

Kephart, "Chlorophyll derivatives—their chemistry, commercial preparation and uses," *Econ. Bot.* 9:3-38 (1955).

Kitamura et al., "Effect of chlorophyllin-chitosan on excretion of dioxins in a healthy man," *Environ Sci Technol* 39(4):1084-1091 (2005).

Kresge et al., "Lyman Creighton Craig: Developer of the Countercurrent Distribution Method," *Journal of Biological Chemistry*, 280(7):127-129 (2005).

Lei et al., "Preparative isolation and purification of acteoside and 2'-acetyl acteoside from *Cistanches salsa* (C.A. Mey.) G. Beck by high-speed counter-current chromatography," *Journal of Chromatography, A* 912(1):181-185, (2001).

Long et al., "Development of an efficient method for the preparative isolation and purification of chlorophyll a from a marine dinoflagellate *Amphidinium carterae* by high-speed counter-current chromatography coupled with reversed-phase high-performance liquid chromatography," *Analytical and Bioanalytical Chemistry*, 386(7-8):2169-74, (2006).

Lu, "Some observations on the deodorant actions of chlorophyllin," *Can Serv Med J* 10:223-232 (1954).

Mata et al., "Effects of chlorophyllin on transport of dibenzo(*a,l*)pyrene, 2-amino-1-methyl-6-phenylimidazo-[4,5-*b*]pyridine, and aflatoxin B$_1$ across Caco-2 cell monolayers," *Toxicology* 196:117-125 (2004).

Morita et al., "Effect of green vegetable on digestive tract absorption of polychlorinated dibenzo-*p*-dioxins and polychlorinated dibenzofurans in rats," *Fukuoka Igaku Zasshi* 90:171-83 (1999).

Nagayama et al., "Promotive excretion of causative agents of Yusho by one year intake of FBRA in Japanese people," *Fukuoka Acta Med* 96(5):241-248 (2005).

Omata & Murata, "Preparation of Chlorophyll *a*, Chlorophyll *b* and Bacteriochlorophyll *a* by Column Chromatography with DEAE-Sepharose CL-6B and Sepharose CL-6B," *Plant and Cell Physiology*, 24(6):1093-1100 (1983).

Reddy et al., "Inhibition of dibenzo[*a,l*]pyrene-induced multi-organ carcinogenesis by dietary chlorophyllin in rainbow trout," *Carcinogenesis* 20(10):1919-1926 (1999).

Simonich "Cancer Prevention by Chlorophylls," http://lpi.oregonstate.edu/fw06/chlorophylls.html, Nov. 2006, accessed Mar. 1, 2007.

Sugiyama et al., "Preventive effects of chlorophyllin fixed on chitosan towards DNA adduct formation of 3-amino-1-methyl-5*H*-pyrido [4,3-*b*]indole in CDF$_1$ mice," *Biol Pharm Bull* 25(4):520-522 (2002).

Sutherland et al., "Review of Progress Toward the Industrial Scale-Up of CCC," *Journal of Liquid Chromatography and Related Technologies* 28:1877-1891 (2005).

Tafesse & Deppa, "Polymetallic complexes in microemulsions for the hydrolysis of 4-nitrophenyl phosphate: a bio-mimetic model for decontamination of organophosphates in the environment," *Ecotoxicol Environ Saf* 58(2)260-266 (2004).

Takahashi & Asada, "Removal of Mn from spinach chloroplasts by sodium cyanide and the binding of Mn$^{2+}$ to Mn-depleted chloroplasts," *Eur J Biochem* 64:445-452 (1976).

Te et al., "In vivo effects of chlorophyllin on the antitumour agent cyclophosphamide," *Int J Cancer* 70(1):84-89 (1997).

Tu & Wang, "Conversion of light into chemical free energy through chlorophyllin-sensitized photoreduction of oxidized nicotinamide-adenine dinucleotide phosphate by cytochrome *c*," *Biochemistry* 8(7):2970-2974 (1969).

Vassilev & Ford, "Poly(propylene imine) Dendrimer Complexes of Cu(II), Zn (II), and Co (III) as Catalysts of Hydrolysis of *p*-Nitrophenyl Diphenyl Phosphate," *Journal of Polymer Science Part A: Polymer Chemistry* 37:2727-2736 (1999).

Wei et al., "Application of analytical and preparative high-speed counter-current chromatography for separation of lycopene from crude extract of tomato paste," *Journal of Chromatography A*, 929:169-173 (2001).

White & Harmon, "Optical solid-state detection of organophosphate using organophosphorous hydrolase," *Biosensors and Bioelectronics* 20:1977-1983 (2005).

Wong & Hsieh, "The comparative metabolism and toxicokinetics of aflatoxin B1 in the monkey, rat, and mouse," *Toxicol Appl Pharmacol* 55(1):115-125 (1980).

Worden et al., "Toxicity Studies on Sodium Copper Chlorophyllin," *British Veterinary Journal* 111:385-387 (1955).

World Health Organization, "Toxicological Evaluation of Some Food Colours, Emulsifiers, Stabilizers, Anti-caking Agents and Certain Other Substances: Chlorophyll Copper Complex and Chlorophyllin Copper Complex, Sodium and Potassium Salts," In: *FAO Nutrition Meetings Report Series* 13th Report of the Joint FAO/WHO Expert Committee on Fodd Additives (1969).

Yun et al., "Non-specific inhibition of cytochrome P450 activities by chlorophyllin in human and rat liver microsomes," *Carcinogenesis* 16(6):1437-1440 (1995).

Alvi, "Screening Natural Products: Bioassay-directed Isolation of Active Component by Dual-mode CCC," *Journal of Liquid Chromatography and Related Technologies*, 24(11&12):1765-1773, (2001).

Anzai et al., "Inhibition of DNA adduct formation and mutagenic action of 3-amino-1-methyl-5H-pyrido[4,3-b]indole by chlorophyllin-chitosan in rpsL transgenic mice," *Jpn. J. Cancer Res.*, 92:848-853, (2001).

Aozasa et al., "Fecal excretion of dioxin in mice enhanced by intake of dietary fiber bearing chlorophyllin," *Bull. Environ. Contam. Toxicol*, 70:359-366, (2003).

Arimoto et al., "Inhibitory effect of hemin, chlorophyllin and related pyrrole pigments on the mutagenicity of benzo[a]pyrene and its metabolites," *Mutat. Res.*, 345:127-135, (1995).

Armbruster et al., "Separation of Crude Plant Extracts with High Speed CCC for Primary Screening in Drug Discovery," *J. Liq. Chrom. & Rel. Technol.*, 24(11&12):1827-1840, (2001).

Breinholt et al., "Chlorophyllin chemoprevention in trout initiated by aflatoxin B$_1$ bath treatment: An evaluation of reduced bioavailability vs. target organ protective mechanisms," *Toxicol. Appl. Pharmacol.*, 158:141-51, (1999).

Breinholt et al., "Dietary chlorophyllin is a potent inhibitor of aflatoxin $B_1$ hepatocarcinogenesis in rainbow trout," *Cancer Res.*, 55:57-62, (1995).

Cho et al., "Chlorophyllin suppression of lipopolysaccharide-induced nitric oxide production in RAW 264.7 cells," *Toxicol. Appl. Pharmacol.*, 166:120-127, (2000).

Chung et al., "Inhibitory effects of chlorophyllin on 7,12-dimethylbenz[a]anthracene-induced bacterial mutagenesis and mouse skin carcinogenesis," *Cancer Lett.*, 145:57-64, (1999).

Courtney et al., "Metal chelate compounds as catalysts in the hydrolysis of isopropylmethylphosphonofluoridate and diisopropylphosphorofluoridate," *Journal of the American Chemical Society*, 79(12):3030-3036, (1957).

Craig et al., "Identification of Small Amounts of Organic Compounds by Distribution Studies—II. Separation by Counter-Current Distribution," *Journal of Biological Chemistry*, 155:519-534, (1944).

Dashwood et al., "Chemopreventive properties of chlorophylls towards aflatoxin $B_1$: a review of the antimutagenicity and anticarcinogenicity data in rainbow trout," *Mutat. Res.*, 399:245-253, (1998).

Dashwood, "Cancer chemoprevention from the food-borne carcinogen 2-amino-1-methyl-6-phenylimidazo[4,5-b]pyridine," *Mutat. Res.*, 405:109-110, (1998).

Egner et al., "Chemoprevention with chlorophyllin in individuals exposed to dietary aflatoxin," *Mutat. Res.*, 523-524:209-216, (2003).

Egner et al., "Chlorophyllin intervention reduces aflatoxin-DNA adducts in individuals at high risk for liver cancer," *Proc. Natl. Acad. Sci.*, 98(25):14601-14606 (2001).

Egner et al., "Identification and characterization of chlorin $e_4$ ethyl ester in sera of individuals participating in the chlorophyllin chemoprevention trial," *Chem. Res. Toxicol*, 13(9):900-906, (2000).

Jubert and Bailey, "Isolation of chlorophylls *a* and *b* from spinach by counter-current chromatography," *Journal of Chromatography A*, 1140:95-100, (2007).

Kelloff et al., "Progress in cancer chemoprevention: development of diet-derived chemopreventive agents," *J. Nutr.*, 130:467S-471S, (2000).

Mata, J. E., "Aflatoxin intervention with chlorophylls: the dark side of peanut butter and the magic of spinach," PowerPoint® presentation, date unknown.

Morita et al., "Chlorophyll derived from Chlorella inhibits dioxin absorption from the gastrointestinal tract and accelerates dioxin excretion in rats," *Environ. Health. Perspect.*, 109(3):289-294 (2001).

Pietrzak et al., "Interactions of chlorophyllin with acridine orange, quinacrine mustard and doxorubicin analyzed by light absorption and fluorescence spectroscopy," *Biophys. Chem.*, 104:305-313, (2003).

Reshetnickov et al., "Novel Drug Form of Chlorin $E_6$," *SPIE*, 3909:124-130, (2000).

Simonich et al., "Natural chlorophyll inhibits aflatoxin $B_1$ induced multi-organ carcinogenesis in the rat," *Carcinogenesis*, (advance access published Feb. 8, 2007).

Sutherland, et al., "Recent Progress on the industrial scale-up of counter-current chromatography," *J. Chrom. A*, 1151:6-13, (2007).

Kasugai, "Studies on the Chlorophyllin Chelate Compounds as the Chemical Protector against Radiation Injury," *Yakugaku Zasshi* 84:1152-1157 (1964).

\* cited by examiner

BEST AVAILABLE COPY

PHARMACEUTICAL FORMULATION COMPRISING A METALOPORPHYRIN AND METHOD FOR ITS PURIFICATION AND USE

REFERENCE TO RELATED APPLICATIONS

This claims the benefit of the earlier filing dates of U.S. Provisional Application No. 60/817,978, filed Jun. 30, 2006, and U.S. Provisional Application No. 60/923,842, filed Apr. 16, 2007, both of which are incorporated herein by reference.

ACKNOWLEDGMENT OF GOVERNMENT SUPPORT

Disclosed embodiments of the present invention were developed, at least in part, using funds provided by grant number CA90890 from the National Institutes of Health. The U.S. Government has certain rights in this invention.

FIELD

The disclosed embodiments of the present invention concern embodiments of a method for isolating a metaloporphyrin, pharmaceutical compositions comprising the metaloporphyrin, and embodiments of a method for making and using the composition.

BACKGROUND

I. Cholinesterase-Inhibiting Phosphoric Ester Poisoning

Among other uses, cholinesterase-inhibiting phosphoric esters are used as insecticides in agriculture. Cholinesterase-inhibiting phosphoric esters also have a toxic effect on human beings. Agricultural workers therefore are subject to periodic acute exposure through inhalation, oral ingestion or percutaneous absorption. As compared to insecticides, the compounds tabun, sarin, soman and VX, nerve warfare agents, are distinguished by a particularly high toxicity. All of these compounds are more or less strong inhibitors of acetylcholinesterase, an enzyme which physiologically blocks the effect of the transmitter acetylcholine released at certain nerve endings. Most poisoning symptoms caused by cholinesterase inhibitors are produced by an inundation with endogenous acetylcholine in the absence of acetylcholinesterase activity.

Currently, the basic drug therapy for such poisonings involves administering parasympatholytic atropine, blocking the exceeding muscarinic acetylcholine effects (e.g., increase of secretion in the respiratory system, bronchospasm, inhibition of the central nervous respiratory drive). There is no suitable antagonist available to normalize the exceeding nicotinic acetylcholine actions (e.g., inhibition of the impulse transmission at the synapses of motorial nerves to the respiratory musculature and to other skeletal muscles up to a complete peripheral motor paralysis). The peripherally caused myoparesis can only be compensated by oximes, e.g., pralidoxime (PAM) or obidoxime (Toxogonin™) which reactivate the inhibited acetylcholinesterase.

Some of the phosphoric cholinesterase inhibitors cleave alkyl residues after accumulation to the acetylcholinesterase, thus stabilizing the bond ("aging"). The aged esterase inhibitor complex cannot be reactivated by oximes. For poisoning by the nerve warfare agent soman, aging occurs after only 2 to 5 minutes. Therapy with atropine and oximes is absolutely insufficient for soman poisoning. The effectiveness of atropine and oximes can be considerably improved by preliminary treatment with indirect parasympathomimetics, e.g., carbamic acid esters, such as pyridostigmine and physostigmine. Carbamic acid esters inhibit the acetylcholinesterase in a manner similar to that of phosphoric esters. However, the bond between the two has a shorter duration and is completely reversible. Because the carbamates inhibit part of the acetylcholinesterase, if dosed suitably, carbamate-inhibited acetylcholinesterases are not available for interaction with phosphoric esters and phosphonates, which have a stronger and prolonged inhibition. This may well be a decisive factor for the protective action of carbamic acid esters, provided that the pretreatment started in time.

Preferably, preventing phosphorylation of the acetylcholinesterase reduces the risk of life threatening effects of exposure to these agents. Physical barriers, including respirators, protective suits, creams or ointments may reduce the likelihood of exposure. Nevertheless, treating a poisoning caused by organophosphorus insecticides requires prompt medical care. Since medical care for harvesters cannot always be accomplished promptly, there is a need for drugs to prophylactically counteract an intoxication. The use of carbamic acid esters for this purpose has already been described (Leadbeater, L. *Chem. in Brit.* 24, 683, 1988). The same applies to the effectiveness of carbamic acid esters in the pretreatment of a soman poisoning in animal experiments (Fleischer, J. H., Harris, L. W. *Biochem. Pharmacol.* 14, 641, 1965, Berry, W. K., Davies, D. R. *Biochem. Pharmacol,* 19, 927, 1970). Effective prophylactic drug dosages must not impair reactivity and functional capacity. However, carbamic acid esters have a low therapeutic index. As compared to pyridostigmine, an increased protective action can be achieved by physostigmine, but the side effects are more severe.

Other approaches include a prophylactic antidote consisting of a combination of pyridostigmine or physostigmine and N-methyl-4-piperidyl-1-phenylcyclopentane carboxylate-hydrochloride or arpenal, sycotrol, carmiphene or benactyzine, and, as an additional compelling component, a tranquilizer, i.e., diazepam or clonazepam. The undesired effects of physostigmine or pyridostigmine cannot be suppressed by the listed parasympatholytics alone. This requires additional administration of tranquilizers, which have problematic side effects.

II. Chlorophyll and Derivatives Thereof

Chlorophyll, and derivatives thereof, have therapeutic value, but typically only as diet ingested materials, or as substantially impure materials. The chemical structures for these compounds are provided below.

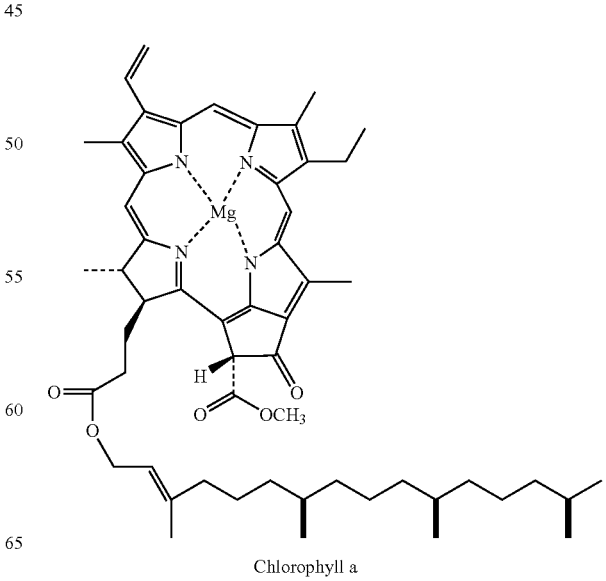

Chlorophyll a

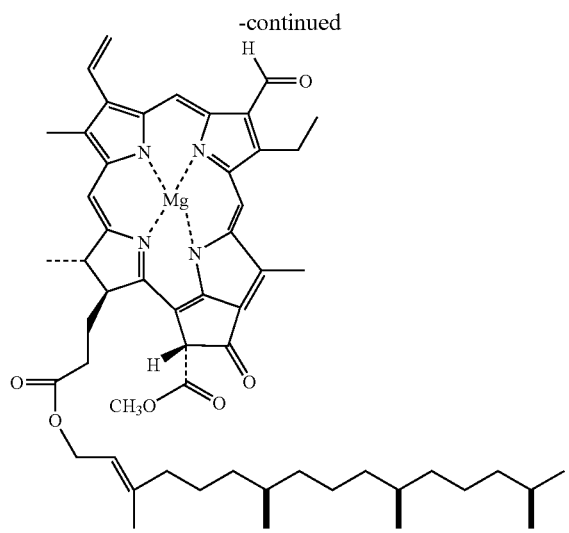

Chlorophyll b

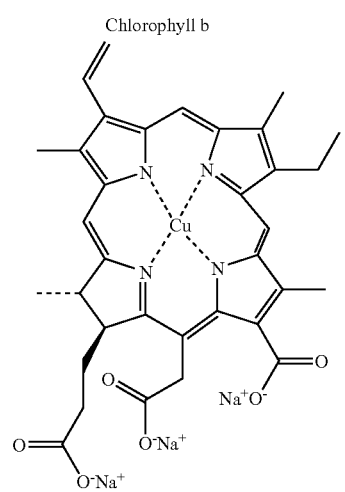

Sodium Copper Chlorophyllin

Evaluating therapeutic results using dietary ingestion, or administration of impure materials, has hindered efforts to assess the effectiveness of such compounds and pharmaceutical compositions comprising such compounds. One reason for this is that chlorophyll is a highly reactive molecule that must be handled with care during isolation procedures. It is susceptible to degradation by light, heat, oxidizing agents, acids and bases. Reactions that typify the sensitivity of chlorophyll include allomerization (oxidation), epimerization, particular at C-13, demetallation, de-phytylation, trans-esterification and decarboxymethylation at C-13. The reactivity of chlorophyll has limited preparatory methods to producing only small quantities of material, and such material typically is not as pure as would be desired.

Nevertheless, some isolation/production technologies have been reported, as indicated by the following excerpt:

In our research into chlorophylls of marine dinoflagellates, chlorophyll a was separated rapidly from the hexane extract of *Amphidinium carterae* in three steps. The first step was silica gel column chromatography, where elution was performed with 0-50% ethyl acetate in n-hexane. The second was high-speed counter-current chromatography using a two-phase solvent system consisting of n-hexane-ethyl acetate-methanol-water (5:5:5:1, v/v), and the third step was preparative reversed-phase high-performance liquid chromatography using a solvent system of acetone-water (89:11, v/v). HPLC analysis showed that the purity of chlorophyll a from the second step was over 83%, and after the third it was over 99%. Thirty milligrams of chlorophyll a was isolated from a crude sample of 250 mg of chlorophylls, and its structure was identified by analyzing its MS, 1H NMR and 13C NMR spectra.

Lijuan Long et al., "Development of an efficient method for the preparative isolation and purification of chlorophyll a from a marine dinoflagellate *Amphidinium carterae* by high-speed counter-current chromatography coupled with reversed-phase high-performance liquid chromatography," *Analytical and Bioanalytical Chemistry*, 386(7-8), 2169-74 (December 2006). This article was published after applicant's priority provisional application, and therefore it should not be construed to be prior art to the present application. Even so, the process disclosed in this publication can be distinguished from disclosed embodiments. This article describes a multi-step process that would not be amenable to commercial production of useful quantities of desired materials. For example, the process involves silica chromatography, followed by counter current chromatography, and finally preparatory high pressure liquid chromatography. Preparative HPLC, which is a known method, alone would have been sufficient to obtain small quantities of material. Preparative HPLC is a tedious procedure. Long et al. also teach using silica gel chromatography, but the silica gel chemically modifies chlorophylls. For example, silica gel has been used to oxidize chlorophylls. Thus, the methodology described in the Long et al. publication likely is not suitable for producing commercially useful quantities of desired materials without the possibility of associated chemical modification of desired products. Moreover, the NMR data provided in this publication does not match the authentic sample of chlorophyll a. As a result, a new method for producing useful quantities of intact materials is still desired.

SUMMARY

The present invention provides a method for producing substantially pure chlorophyll (Chl), and derivatives thereof (including by way of example and without limitation, sodium copper chlorophyllin (CHL)) and compositions comprising chlorophyll, and derivatives thereof. Certain disclosed embodiments comprise purifying chlorophyll from a material containing chlorophyll and other compounds using centrifugal partition chromatography. In a particular embodiment of the method, bulk liquid/solid extraction of the chlorophyll-containing material (such as algae, alfalfa, spinach or a *Spirulina* organism) is followed by a liquid/liquid washing of the extract. The resultant mixture of chlorophylls and other compounds is then subjected to centrifugal partition chromatography, particularly counter current chromatography, to produce chlorophyll that is preferably greater than 92% pure, and more preferably greater than 95% pure. Once obtained, the substantially pure chlorophyll may be converted to substantially pure derivatives thereof. This particular embodiment is substantially more amenable to scale up than other known chromatographic techniques, such as preparative high performance liquid chromatography (HPLC). Such highly purified chlorophyll and chlorophyll derivatives provide substantially enhanced therapeutic results relative to those of standard purity.

Furthermore, the present invention provides a therapeutic, or a therapeutic formulation, comprising chlorophyll and/or derivatives thereof, particularly such compounds that are produced by counter current chromatography. Disclosed therapeutic(s), or therapeutic formulations thereof, are useful for the prophylaxis, preliminary treatment, or treatment of a poisoning caused by organophosphorus cholinesterase inhibitors, vesicating agents, polycyclic aromatic hydrocarbon, fungal toxins, such as those of aflatoxin B1, or combinations of said poisons. Disclosed embodiments of the invention can be used as a "broad spectrum" medical intervention for treating either single or multi-agent exposure. Examples of organophosphorus cholinesterase inhibitors include esters of phosphoric acid derivatives, e.g., nitrostigmine (diethyl-(4-nitrophenyl)-thiophosphate, better known under the names Parathion or E 605), but they also include tabun, difluorophane (G-agent) as well as the phosphonic acid derivatives sarin, soman, and VX. Examples of vesicating agents include esters of nitrogen mustards. Examples of polycyclic aromatic hydrocarbon include dibenzo(a,l)pyrene, benzopyrene, 2-Amino-1-methyl-6-phenylimidazo[4,5-b]pyridine (PhiP).

Certain disclosed embodiments of a method for making a chlorophyll or chlorophyllin therapeutic involve obtaining from a suitable source, such as algae, alfalfa or spinach, a starting material for conversion to chlorophyllin that is greater than 90% chlorophyll a or a'. Particular embodiments concern obtaining a starting material from *Spirulina pacifica*. Obtained chlorophyll is then formulated as a therapeutic, or a therapeutic composition or subsequently transformed to a chlorophyll derivative, such as chlorophyllin. Obtaining starting material may comprise first extracting chlorophyll from a suitable source to produce a fraction substantially enriched in chlorophyll, and then purifying the fraction using counter current chromatography. As chlorophyll is light sensitive, disclosed process embodiments may be advantageously performed in dim light or no light conditions.

Disclosed pharmaceutical formulations comprise an effective dose of a substantially pure chlorophyll therapeutic, chlorophyllin therapeutic, or derivative thereof. The therapeutics are substantially more pure, and hence more effective, than prior known compounds as a result of using counter current chromatography to produce the purified therapeutic. Particular disclosed embodiments concern a pharmaceutical formulation comprising an extracted, purified and chemically modified chlorophyllin, such as may be obtained from *Spirulina pacifica*, particularly formulations comprising at least 90% chlorophyllin, even more preferably comprising at least 94% chlorophyllin, with a particular example comprising a substantially spectroscopically pure form of sodium copper chlorophyllin. Particular embodiments concern a pharmaceutical formulation comprising a sufficient amount of a spectroscopically pure form of sodium copper chlorophyllin to provide a dose of from about 5 mg/kg of kg body-weight to about 20 mg/kg of kg body-weight. Solely by way of example, the composition can comprise CHL such that administration provides a relatively high dose of from greater than 0 mg/kg body-weight to about 15 mg/kg body-weight CHL.

A person of ordinary skill in the art will appreciate that therapeutic formulations often include a compound or compounds other than a primary therapeutic. Disclosed therapeutic formulations therefore may include at least one additional excipient, therapeutic or diagnostic agent. For example, the pharmaceutical formulation may further comprise a plasticizer, a pH adjuster, a GI motility adjuster, a viscosity adjuster, a therapeutic agent, a diagnostic agent, an expansion agent, a surfactant, fillers or extenders, binders, humectants, disintegrating agents, solution retarding agents, absorption accelerators, wetting agents, absorbents, lubricants, dissolution aids, and mixtures thereof. Moreover, disclosed compounds and compositions comprising such compounds can be formulated as desired, including: as a solid dosage form; a liquid dosage form; an oral dosage form; a chewable formulation; a controlled release formulation; prophylactic oral dosage forms that provide controlled therapeutic release over at least one day; an oral/buccal formulation containing active substances in a manner showing rapid absorption and adherence to oral mucosal membranes for treating acute poisoning or impending risk of exposure to toxins; and inhaled dosage form suitable for direct application to the respiratory tract and to lung tissue. Therapeutic compositions also can be formulated for treating particular subjects, such as humans and animals, or for treating exposure to particular toxins. By way of example, disclosed chlorophyllin compositions can comprise montmorillonite clay for treating exposure to aflatoxin.

Disclosed embodiments also concern a method for treating exposure to a toxin. One disclosed embodiment comprises administering to a subject a pharmaceutical formulation comprising an effective amount of a therapeutic comprising a purified and chemically modified chlorophyllin. Particular embodiments concern administering pharmaceutical formulations comprising a substantially pure chlorophyllin or derivative thereof, such as sodium copper chlorophyllin, purified using counter current chromatography. The method may involve maintaining sufficient therapeutic serum levels to effectively treat exposure to the toxin.

Certain embodiments concern treating acute exposure to a toxin, while other embodiments concern treating chronic exposure to a toxin. For example, disclosed embodiments of the method comprise identifying humans exposed to a neurotoxic agent, toxic metals, a metabolic toxin, a vesicating agent, cancer causing agents, polycyclic aromatic hydrocarbons sarin, soman, a sulfa mustard, and/or aflatoxin, and administering the composition to those humans identified as being exposed. Disclosed embodiments also concern prophylactic administration. Where the toxin is a vesicating agent, it may be advantageous to administer a composition as an inhaled dosage form, as a chewable dosage form, or both. Where the toxin is a mustard gas or similar toxic agent, a composition may be advantageously administered as an inhaled dosage form. For exposure to a cancer causing agent the composition may be advantageously administered as a cancer chemopreventive agent.

The foregoing and other objects, features, and advantages of the invention will become more apparent from the following detailed description, which proceeds with reference to the accompanying figures.

DETAILED DESCRIPTION

I. Terms

Figure 1:
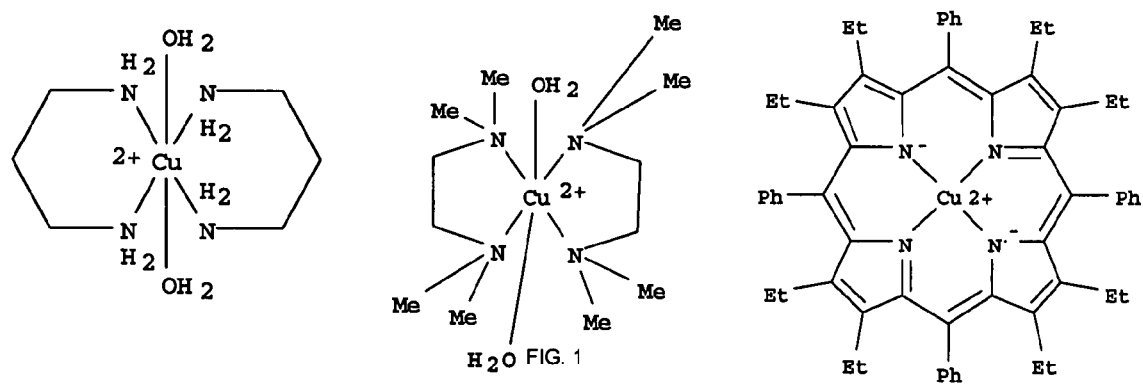
FIG. 1 illustrates copper-containing compounds capable of catalyzing hydrolysis of organophosphates: 1,3-Propanediamine, copper complex; 1,2-Ethanediamine, N,N,N',N'-tetramethyl-, copper complex; (2,3,7,8,12,13,17,18-Octaethyl-5,10,15,20-tetraphenylporphyrinato)copper.

Unless otherwise noted, technical terms are used according to conventional usage. The singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. All publications, patent applications, patents, and other references mentioned herein are incorporated by reference in their entirety, unless the context clearly indicates otherwise. In case of conflict, the present specification, including explanations of terms, will control. Although methods and materials similar or equivalent to those described herein can be used in the practice or testing of the present disclosure, suitable methods and materials are described below. The materials, methods, and examples are illustrative only and not intended to be limiting.

The following explanations of specific terms are provided to facilitate review of the various examples of this disclosure:

Active agent: Any therapeutic or diagnostic agent now known, produced according to disclosed embodiments or hereinafter discovered that can be formulated as described herein. Examples of therapeutics, without limitation, are listed in U.S. Pat. No. 4,649,043, which is incorporated herein by reference. Additional examples are listed in the American Druggist, p. 21-24 (February, 1995).

Derivative or Mimetic: A derivative is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. A molecule that differs from the parent compound by the absence of functional groups, or the transformation of one functional group to another is also a derivative. A molecule with replacement substituent atoms is also a derivative. For example, chlorophyllin is a derivative of chlorophyll, as the ester groups have been saponified to produce carboxylic acid or carboxylate functional groups, at least one of the pentyl rings has been opened to provide additional carboxylic acids or carboxylate functional groups, and the central magnesium atom has been replaced with copper. Homopolymers (e.g. chlorophyll-chlorophyll) and heteropolymers (e.g. chlorophyll-chlorophyll derivative) of a parent compound also are derivatives of that parent compound. Structural derivatives are often found using quantitative structure activity relationships (QSAR), with techniques such as those disclosed in Remington (*The Science and Practice of Pharmacology*, 19th Edition (1995), chapter 28). A mimetic is a molecule that mimics the activity of another molecule, such as a biologically active molecule. Biologically active molecules can include chemical structures that mimic the biological activities of a compound.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Controlled release: Includes timed release, sustained release, pulse release, delayed release and all terms which describe a release pattern other than immediate release.

Centrifugal Partition Chromatography (CPC): A chromatographic technique that uses a coil filled with two immiscible liquids on a rotating plate. The hydrodynamic forces created by rotation effect partitioning of compounds dissolved in the liquids. A particular kind of CPC is counter current chromatography. Where one of the fluids flows through the tubing during rotation.

Diagnostic: A material useful for testing for the presence or absence of a material or disease, and/or a material that enhances tissue or cavity imaging.

Effective amount: An amount of a diagnostic or therapeutic agent that is useful for producing a desired effect.

Inhibiting or Treating a Disease: Inhibiting the full development of a disease or condition, for example, in a subject who is at risk for a disease. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Liquid dosage forms: Include dosage forms suitable for oral administration, including by way of example and without limitation, pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavouring and perfuming agents. Suspensions, in addition to the active compounds, may contain suspending agents such as ethoxylated isostearyl alcohols, polyoxyethylene sorbitol and sorbitan esters, microcrystalline cellulose, aluminium metahydroxide, bentonite, agar-agar, and tragacanth and mixtures thereof.

Mammal: This term includes both human and non-human mammals. Similarly, the term "subject" includes both human and veterinary subjects.

Pharmaceutically acceptable: Compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. "Pharmaceutically acceptable" includes acceptability for both human and veterinary purposes, of which acceptability for human pharmaceutical use is preferred.

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material.

Solid dosage forms: Includes forms suitable for oral administration, including by way of example, and without limitation. capsules, tablets (also called pills), powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules and tablets, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, the oral formulations may contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

Oral formulations also may contain such agents designed to improve stability of chlorophyll or its derivatives, such as ascorbate esters.

Spectroscopically Pure: A compound is considered spectroscopically pure when there is substantially no contamination by visual inspection of at least one spectrum. This typically corresponds to mass contamination constituting less than 5%, preferably less than 2% and more preferably less than 1%. Spectroscopic techniques useful for assessing purity include, without limitation, UV/Vis spectroscopy, nuclear magnetic resonance (NMR) and high resolution mass spectroscopy.

Therapeutically Effective Amount: A quantity of a specified agent sufficient to achieve a pharmacologically desired effect in a subject being treated with that agent. For example, this may be the amount of a metallopophyrin useful in increasing resistance to, preventing, ameliorating, and/or treating exposure to a toxin. Ideally, a therapeutically effective amount of an agent is an amount sufficient to increase resistance to, prevent, ameliorate, and/or treat infection and without causing a substantial cytotoxic effect in the subject. The effective amount of an agent useful for increasing resistance to, preventing, ameliorating, and/or treating infection and disease in a subject will be dependent on the subject being treated, the severity of the affliction, and the manner of administration of the therapeutic composition. Actual dosage levels of active ingredients in the pharmaceutical compositions may be varied so as to obtain an amount of the active compound(s) that is effective to achieve the desired therapeutic response for a particular patient, composition, and mode of administration. The selected dosage level will depend upon the activity of the particular compound, the severity of the condition being treated and the condition and prior medical history of the patient being treated. A person of ordinary skill in the art will know how to start doses of the compound at levels lower than required for to achieve the desired therapeutic effect and to gradually increase the dosage until the desired effect is achieved.

II. Compounds and Compositions

Disclosed embodiments of the present invention concern therapeutic compositions comprising chlorophyll or chlorophylls, CHL, derivatives of chlorophyll, and combinations thereof. Chlorophylls and CHL are plant pigments commonly found in the human diet which have been shown to exert anti-cancer effects in vivo (Dashwood 1997; Egner et al. 2001). CHL are semi-synthetic, water-soluble sodium-copper salts of chlorophylls that are used as food colorants and that also are marketed as an over-the-counter (OTC) drug for treating body, urinary and fecal odor (Derifil™) and as an accelerant for wound healing (Panafil™) (Hainer 1954; Kephart 1955; Lu 1954). CHL is a mixture of Cu(II)chlorins which include the Cu(II)chlorin e6, Cu(II)chlorin e4 and Cu(II)chlorin ethyl ester derivatives.

Certain disclosed compositions include at least one highly purified, e.g., greater than 90% pure, preferably greater than 95%, and even more preferably spectroscopically pure, compound having either Formula 1 or Formula 2, as shown below:

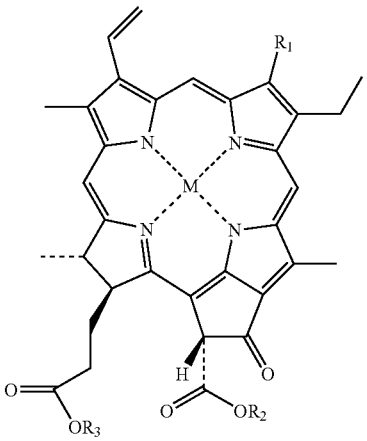

Formula 1

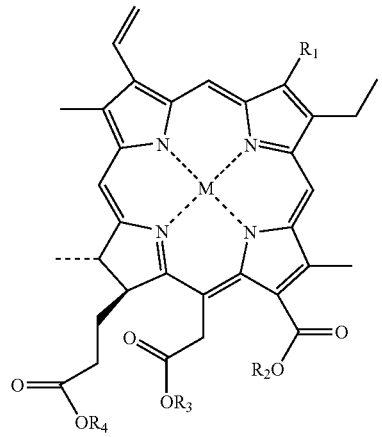

Formula 2

With reference to Formulas 1 and 2, M refers to a metal ion with a charge of +2 selected from beryllium, magnesium, calcium, strontium, barium, chromium, manganese, iron, cobalt, nickel, copper, zinc, molybdenum, technetium, ruthenium, rhodium, palladium, cadmium, tungsten, rhenium, osmium, iridium, platinum, and mercury. Metal cations with +1 or +3 charges also could be used, though this would produce a complex with either a −1 charge (if the metal has a charge of +1) or +1 (if the metal has a charge of +3). A person of ordinary skill in the art would be able to balance any such overall charge with an appropriate counter ion or ions. $R_1$ typically is an aliphatic moiety, such as a hydrocarbon or hydrocarbon chain, lower (fewer than 10 carbon atoms) alkyl groups, such as methyl and ethyl, or a carbonyl bearing moiety, such as an aldehyde, ketone or ester. $R_2$-$R_4$ independently are aliphatic chains, typically having 20 carbon atoms or fewer, particularly alkyl groups, and even more particularly alkyl groups having 20 or fewer carbon atoms in the chain, including lower (fewer than 10 carbon atoms) alkyl groups. The hydrocarbon chain may be saturated or unsaturated; interrupted by heteroatoms such as N, O and/or S; contain saturated or unsaturated cyclic structures, in the chain or pendent to the chain, with or without heteroatoms; or contain functional groups including by way of example and without limitation, hydroxyls, amines, aldehydes, carboxylic acids, esters, ethers, epoxides, ketones, thiols, sulfides, phosphines and phosphates. $R_2$-$R_4$ also may be biologic moieties. For example, $R_2$-$R_4$ may comprise a carbohydrate, lipid, steroid, amino acid, peptide, protein, nucleoside, nucleotide, oligonucleotide, oligonucleoside, or nucleic acid (including DNA and RNA). $R_2$-$R_4$ also can be positively charged species, such as metal ions with a charge of +1 selected from lithium, sodium, potassium, cesium, chromium, manganese, iron, cobalt, nickel, copper, zinc, molybdenum, technetium, ruthenium, rhodium, palladium, silver, cadmium, tungsten, rhenium, osmium, iridium, platinum, gold, and mercury; or a non-metallic cation with a charge of +1 such as ammonium. A metal or non-metallic cation with a charge of +2 or +3 also could be used, though it would produce a complex with an overall charge. A person of ordinary skill in the art would be able to balance such charge with an appropriate counter ion or ions.

Certain disclosed embodiments concern therapeutic formulations, particularly formulations comprising chlorophylls or chlorophyllin, particularly chlorophyllin having substantially pure chlorophyll a or a', such as at least about 90%, and preferably at least about 94%, with typical purities ranging from about 94% to about 98% chlorophyll a or a'. Empirical data presented herein establishes that substantially pure chlorophyll is a better therapeutic for cancer than less pure therapeutics. For example, chlorophyll having a purity of 97% is substantially more efficacious for treating cancer than chlorophyll having a purity of 90%. Working Example 5 shows a large unexpected decrease in the tumor prevalence in trout when treated with substantially pure chlorophyll as opposed to ordinary purity chlorophyll; an increase in purity of only 7% approximately decreases the cancer rate in trout by a factor of 2. Disclosed therapeutic formulations include at least one active ingredient, and may include a mixture of active agents, including a mixture of chlorophyllin active agent(s), or a chlorophyll or chlorophyllin active agent and at least one additional therapeutic, diagnostic or other agent. The active ingredient may be released (1) in a manner such that all is released very rapidly or (2) some or all is released slowly or (3) is time delayed.

Disclosed embodiments comprising chlorophyll/chlorophyllin-based formulations may further comprise other materials commonly used in pharmaceutical formulations, such as other active/therapeutic agents and/or excipients. Examples of such materials include, but are not limited to, a plasticizer, a pH adjuster, a GI motility adjuster, a viscosity adjuster, a therapeutic agent, a diagnostic agent, an expansion agent, a surfactant, fillers or extenders, binders, humectants, disintegrating agents, solution retarding agents, absorption accelerators, wetting agents, absorbents, lubricants, dissolution aids, and mixtures thereof.

The therapeutic may be provided in any suitable form, such as solid dosage forms, liquid dosage forms, inhalants, etc. Beads comprising therapeutics, or therapeutic formulations, may be made using well known methods such as spheronization or marumerization. These and similar techniques can be used to produce, for example, a bead core that is highly drug loaded, or a sugar or other substance without any drug may be used as the starting core. Therapeutic may be "buried" in the core or applied to any number of layers closer to the surface as desired.

Therapeutic agents/compositions of the present invention can be administered by any suitable method. For example, the therapeutic agent, or composition comprising the therapeutic agent, may be administered, by way of example and without limitation, as a tablet, capsule, powder, bead, pellet, granules, solid dispersion, soft chew formulation, as an inhalant, etc., or combinations thereof. Administration to a subject can be by any suitable means including, but not limited to, orally, rectally, nasally, and/or vaginally. Active compounds, or compositions comprising active compounds, may be given as a single dose, in multiple doses or as a sustained release formulation.

Therapeutics, or therapeutic formulations should be administered to provide a relatively high dose of from greater than 0 mg/kg body-weight, typically about 0.5 mg/kg body weight, up to at least about 20, and more typically from about 1 mg/kg body-weight to about 15 mg/kg body-weight CHL, and even more typically from about 3 to about 5 mg/kg body-weight CHL.

III. Therapeutic Uses

Sodium copper chlorophyllin has demonstrated properties in animal and in human studies that suggest a possible role as an interceptor molecule that can reduce the risk of toxicity and long term effects of biological and chemical agents. However, inconsistent and unreliable production of chlorophyllin products produce inconsistent results. Disclosed embodiments of the present invention concern a method of reducing the bioavailability or toxicity of a broad range of toxins using a highly pure formulation of chlorophyll or chlorophyll derivatives. Purified chlorophyll, or derivatives thereof, or compositions comprising purified chlorophyll, or derivatives thereof, are suitable for use as a medical intervention to prevent acute and chronic effects of toxic substances. This method is scaleable and substantially improves medical interventions for at least those toxicities specifically identified herein. The pharmaceutical formulation is of a substantially different chemical makeup and higher purity than known compositions.

As stoichiometric scavengers, derivatives of chlorophylls have a unique chemical composition to bind or deactivate broad classes of chemical and biological agents (CB) and metals, and may provide an affordable and highly effective medication for treating exposure to multiple toxic agents. Although there are few studies that have tested the efficacy of CHL as a treatment for acute exposure to nerve and vesicating agents, several studies suggest that this approach may be feasible. Chlorophyllins have a proven safety history and are frequently present in the body. Chlorophyllins are a mixture of chlorins that have demonstrated a remarkable ability to complex with toxins and polycyclic aromatic hydrocarbons (PAHs) (Dashwood & Liew 1992; Dashwood 1997; Egner et al. 2003; Mata et al. 2004; Simonich et al., 2007). Further, these molecules chelate metals providing a possible medical intervention for radiation poisoning (Kasugai 1964). Well-controlled studies of the effectiveness of CHL as a medical countermeasure for prophylaxisis or treatment of acute exposure to chemical and biological agents are lacking.

A number of studies have characterized interactions of CB and CHL (See Table 1). However, the use of CHL as a "broad-spectrum" medical countermeasure was not conceivable without the enabling discovery of its actions against several classes of CB.

Many commercial over-the-counter (OTC) products and common food dyes contain significant amounts of CHL.

However, these formulations are complex mixtures of chlorins along with other impurities and oxidation products. The methods described herein produce substantially spectroscopically pure forms of chlorophylls, and their derivatives, such as sodium copper chlorophyllin, suitable for use as a medical countermeasure to a number of important toxins and chemicals. The purity of the chlorophylls and their derivatives also may be assessed by elemental analysis. Derivatives of chlorophylls, generally mixtures of chlorins found commonly in food colorings and in over-the-counter dietary supplements, recently have been found to be effective "interceptor molecules" for reducing exposure to a number of carcinogens. The bioavailability of these molecules commercially available as crude mixtures of CHL has been recognized for nearly 80 years (Harrison et al. 1954; Kephart 1955). However, the utility of chlorophyllins as interceptor molecules is only beginning to be understood. A recent report by Egner et al. suggests that these molecules can reduce the number of DNA adducts in humans exposed to aflatoxin $B_1$ (Egner et al. 2003; Egner et al. 2000; Egner et al. 2001). Many other effects of CHL have been reported for a variety of chemicals categorized as mid- and high-priority agents, including derivatives of mustine gas (cyclophosphamide) (Abraham et al. 1994; Te et al. 1997). A list of potential therapeutic applications of CHL is provided in Table 1.

TABLE 1

Known chemical and biological targets for CHL complexation or scavenging.

| Agent | Use | Reference |
|---|---|---|
| aflatoxin $B_1$ | interceptor molecule, antimutagen | (Dashwood et al., 1991; Breinholt et al., 1995; Dashwood et al. 1998; Egner et al. 2000; Egner et al. 2001; Mata et al. 2004) |
| dibenzo(a, i)pyrene | interceptor molecule, antimutagen | (Harttig et al., 1998; Mata et al. 2004) |
| 2-amino-1-methyl-6-phenylimidazo-[4,5-b]pyridine (PhIP) | interceptor molecule, antimutagen | (Dashwood 1997) |
| 3-amino-1-methyl-5h-pyrido[4,3-b]indole | Antimutagen | (Anzai et al. 2001) |
| hexachlorodibenzo-p-dioxin(s) | Binder | (Aozasa et al. 2003) |
| Dioxins | Binder | (Kitamura et al. 2005; Morita et al. 1999; Morita et al. 2001) |
| Quinacrine | interceptor molecule, antimutagen | (Arimoto et al. 1993; Pietrzak et al. 2003) |
| Doxorubicin | interceptor molecule, antimutagen | (Pietrzak et al. 2003) |
| 2-methoxy-6-chloro-9-[3-(ethyl-2-chloroethayml)i nopropylaminolacridine HCI (ICR-170) | interceptor molecule, antimutagen | (Arimoto et al. 1993) |
| 3-amino-1,4-dimethyl-5H-pyrido[4,3-b]indole (Trp-P-1) | interceptor molecule, antimutagen | (Arimoto et al. 1993) |
| 3-amino-1-methyl-5H-pyrido[4,3-b]indole (Trp-P-2) | interceptor molecule, antimutagen | (Arimoto et al. 1993) |
| Chlordane | Interceptor molecule | (Sarkar et al. 1993) |
| benzo[a]pyrene | interceptor molecule, antimutagen | (Arimoto et al. 1995; Tachino et al. 1994) |
| polio virus | interceptor molecule | (Botelho et al. 2004) |
| lipopolysaccharide (LPS) | anti-oxidant | (Cho et al. 2000) |
| 7,12-dimethylbenz[a]anthracene | chemopreventive | (Chung et al. 1999) |
| 2-amino-3-methylimidazo[4,5-f]quinoline (IQ) | interceptor molecule, antimutagen | (Dashwood & Guo 1992) |
| 1-nitropyrene, 1,6-dinitropyrene or 1,8-dinitropyrene (and urban air particulates) | antimutagen | (Espinosa-Aguirre et al. 1993) |
| cesium chloride, mercuric chloride and cobalt chloride (heavy metal poisoning) | possible interceptor | (Ghosh et al. 1991) |
| radiation poisoning | isotope chelator | (Kasugai 1964) |
| photodynamic therapy (PDT) | photosensitizer | (Tu & Wang 1969) |
| chromium (VI) oxide | antimutagen | (Sarkar et al. 1993) |

A. Neurotoxic Agents:

While there are many reports of CHL interactions with a variety of biological and chemical agents, there are no reports that have investigated the possibility that CHL can be used as a medical countermeasure for acute exposure to chemical agents. The sodium copper form is particularly important because two highly toxic phosphofluoridates, Sarin and Soman, are completely hydrolyzed in the presence of various Cu(II) diamine complexes within one minute at room temperature (Courtney 1957). It was recognized early on by Gustafson et al. that cis-diaqua copper complexes efficiently hydrolyze phosphonate esters (Gustafson & Martell 1962). However, a major problem with cis-diaqua metal complexes is that they form inactive dimers (Gustafson & Martell 1960). More recently, Cu(II)-containing dendrimers have been developed as potential catalysts for degradation of organophosphate insecticides and nerve agents. The hydrolysis rates for these compounds were less effective than other agents such as metallomicelles (Vassilev 1999). Copper (II) has also been used in oil and water emulsions for possible use in the decontamination of areas exposed to pesticides or nerve gas (Tafesse & Deppa 2004).

Lack of investigation in this area may be due, in part, to the relatively recent discovery that these compounds can reduce systemic bioavailability of toxins (Hayashi et al., 1999; Simonich et al., 2007) and that specific chlorins can be measured in serum (Egner et al. 2000). White et al., using similar Cu(II)-containing porphyrin (See FIG. 1, for one example) demonstrated interactions between organophosphates and copper metaloporphyrins for detecting organophosphates in analytical systems (White & Harmon 2005). This work also demonstrated that the copper was critical to the interaction, and that the a-metallic porphyrin did not interact with the organophosphate. However, this study characterized this interaction as part of diagnostic method for detecting organophosphates rather than as a medical countermeasure. The authors did not envision using these compounds, nor did they predict an effective plasma concentration of copper metalloporphyrin that would enable these compounds to be used as medical countermeasures to organophosphate poisoning. While these compounds have been known to be bioavailable and have been reported to turn tissues green, researchers have not appreciated possible medical uses for CHL beyond its use as an internal deodorant until recently (Harrison et al. 1954; Kephart 1955).

The use of metal compounds as catalysts in the hydrolysis of sarin and bis(1-methylethyl) phosphorofluoridate (DFP) was reported by Courtney et al. (Courtney 1957). In these studies, researchers found that Cu(II) chelates were the most effective catalysts because more electropositive compounds are relatively more reactive. This observation has been applied to Cu(II) containing materials that are capable of increasing the rate of hydrolysis of soman and DFP (Hammond & Forster 1991). The in vitro rates of hydrolysis of some of the compounds tested are relatively slow. This would suggest that they might be less potent or ineffective as interceptor molecules for the very fast acting nerve agents. However, as a pharmacological agent, CHL can be given at much higher doses to achieve substantial concentrations in tissues and plasma with no apparent toxicity. Thus, one embodiment of the present invention concerns administering high stoichiometric ratios of CHL relative to toxin to provide substantial protection for acute exposure. The levels of CHL that can be achieved systemically would not be practical for other chelated forms of Cu(II) that would be expected to have adverse systemic effects at high concentrations in the plasma. For example, the standard treatment for nerve agent poisoning, atropine, produces a number of side effects at high concentrations. In rodents, treatment with atropine following exposure to soman is generally supportive. Effective atropine doses do provide some symptomatic relief, but the animal eventually succumbs to the nerve agent (Mata, personal observation). CHL should substantially increase the rate of hydrolysis of organophosphate, and therefore its use could provide a low cost alternative to less effective or less available treatments.

B. Proposed Mechanism

Figure 2:
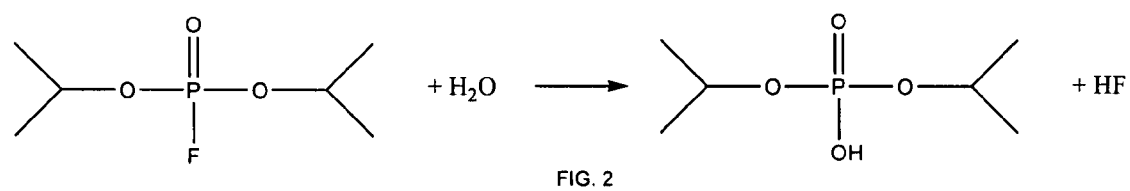
FIG. 2 schematically illustrates the slow hydrolysis of DFP in water.

The hydrolysis of DFP (FIG. 2) is slow in water and yields two equivalents of acid; i.e., di-isopropyl phosphate and HF. Without limiting the present invention to a theory of operation, one proposed mechanism suggests that ingested CHL promotes DFP hydrolysis and consequently eliminates its powerful cholinesterase inhibition. The central copper atom of CHL is not coordinately saturated; therefore, one or two axial ligands may bind to the metal. The strength of this binding depends in part on the nucleophilicity of the ligand. In aqueous systems, water molecules, in general, surround the cations of the 3d transition metals. A ligand added to the solution of a hydrated metal cation may replace the water molecule of the aqua complex.

Figure 3:
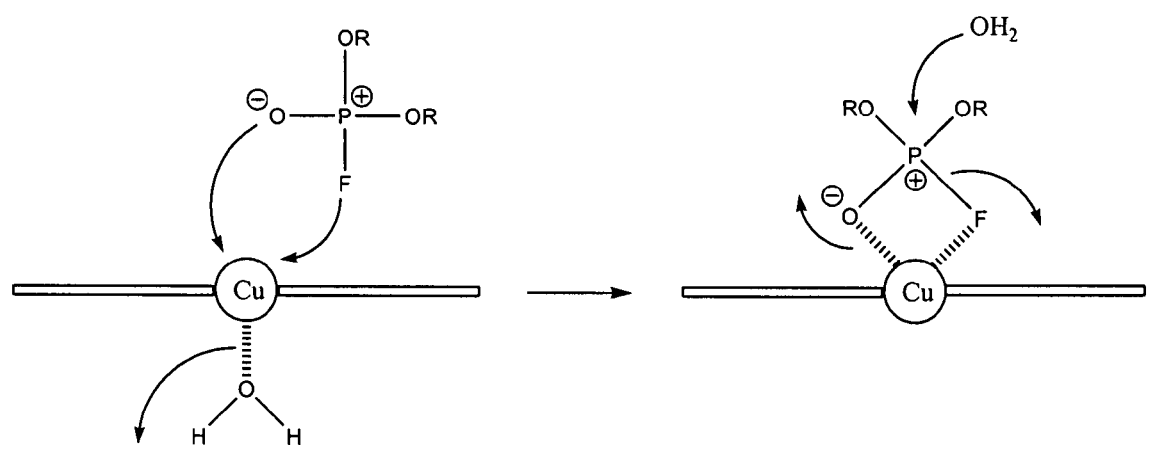
FIG. 3 illustrates a proposed mechanism for hydrolysis of DFP by CHL.
Figure 4:
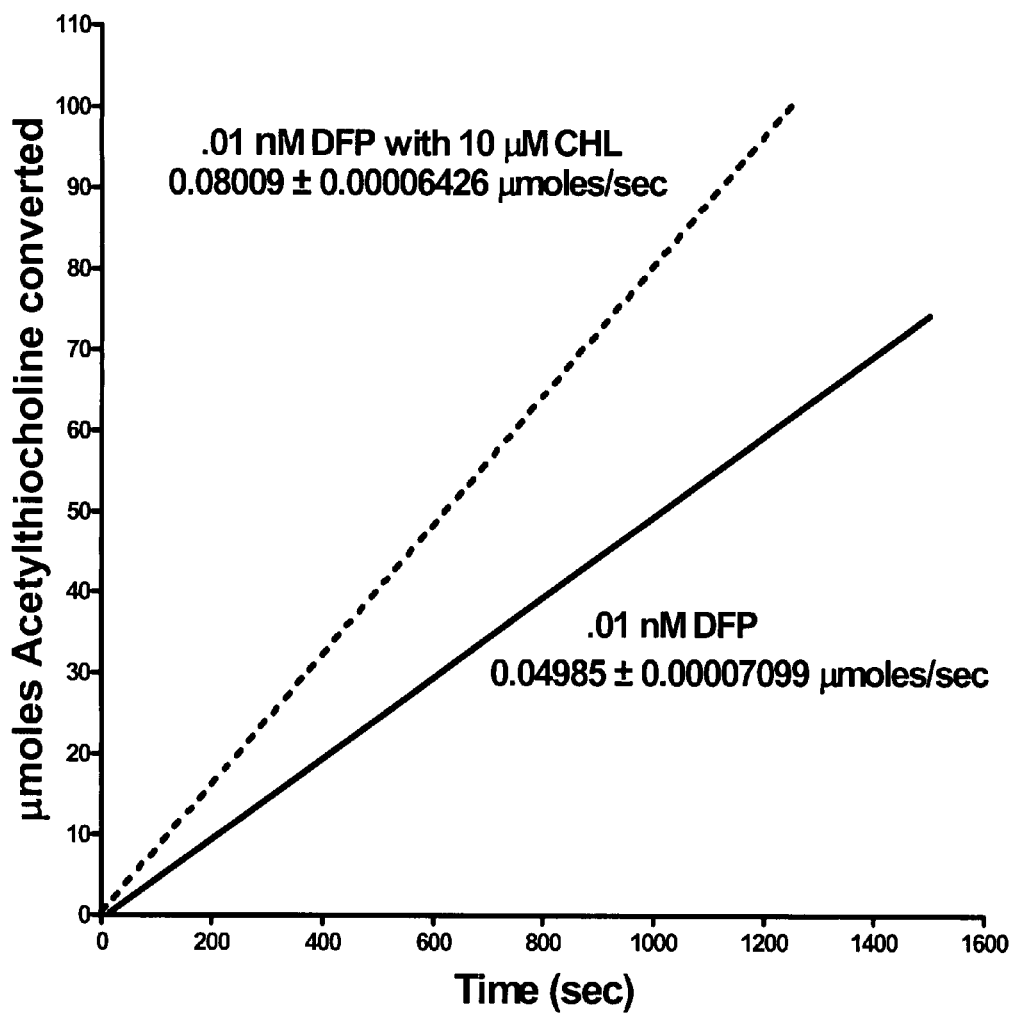
FIG. 4 is a graph of the quantity of acetylthiocholine processed by acetylcholinesterase versus time demonstrating disinhibition of acetylcholinesterase by DFP in the presence of CHL.

A proposed mechanism for the catalyzed hydrolysis of DFP by CHL is provided by FIG. 3. The result is the substitution of the water molecule by the new ligand, HF. The stability of the metal chelate compound formed should be sufficiently high that it will not appreciably dissociate at physiological pH. This assumption is based on showing that Cu(II) chelates promotes the hydrolysis of Sarin and DFP in a 1:1 molar ratio (Courtney et al. 1957). In order for the dissociation rate of the fluoride ion to be increased, it is necessary that the metal ion lowers the transition state energy by co-ordination of the partially ionized fluorine atom. It is evident that the more electropositive the Cu(II) atom is, the greater its effect on the acceptor activity of the phosphorus atom. The resulting diisopropylphosphate generated by the hydrolysis no longer inhibits acetylcholinerserase (Imaizumi et al. 1993). In any event, CHL significantly disinhibits acetylcholinesterase resulting in a 50% increase in the rate of substrate turnover when CHL was present compared to the DFP inhibited enzyme (see FIG. 4).

C. Vesicating Agents

The observation that soldiers accidentally subjected to sulfa mustards during World War I had smaller lymph nodes eventually led to the development of a variety of alkylating agents useful for treating cancers. These chemicals, like vesicating agents deployed in WWI, are very toxic with a narrow margin of safety. Efforts to decrease the toxicity of alkylating agents include the use of CHL as an interceptor molecule capable of reducing the effects of chemotherapy in cancer patients (Abraham et al. 1994; Te et al. 1997). Abraham et al. reported that the protective effects of CHL were dose dependent for two alkylating agents, cyclophosphamide and nitrosourea, as well as urethane and gamma radiation (Abraham et al. 1994). These studies were not intended to test the hypothesis that CHL would be protective in acute exposure. CHL would be important in the arsenal because the lethal effects of sulfa mustards are dependent on concentration and the time of exposure. In a mass casualty scenario, it would be likely that a large number of affected people would be evacuated and exposure although possibly lethal could be treated. A safe, effective oral dosage form that could be distributed to those who are not completely incapacitated by the vesicating agent could reduce the toxicity, potentially saving many lives following a release of a vesicating agent. The preferred use of CHL would be as a prophylactic, however, due to the possible benefits of having CHL present in bodily fluids. Studies in mice that investigated the use of oral CHL in combination with cyclophosphamide found that combinations were antimutagenic as measured by the Salmonella/microsome assay. This also was demonstrated by a reduction in micronuclei in bone marrow polychromatic erythrocytes in response to co-treatment with both agents. Experiments utilized CHL administered either in drinking water (1%) for 2 days before treatment, or by gavage (200 mg/kg) 2 hours before treatment with cyclophophamide (220 mg/kg) (Te et al. 1997). These studies suggest that there may be a role for CHL for treating exposure to vesicating agents. Further, these studies also demonstrate that oral administration of CHL is effective against systemic toxicity. This is important in the development of CHL for prophylactic administration or dosage directly preceding the exposure.

An obvious shortcoming of a systemic dosage form is the fact that vesicating agents can produce significant contact injury because they are so reactive and tend to blister (thus the characterization as "blistering agents"). In the form of gas or liquid, a mustard agent attacks the skin, eyes, lungs and gastro-intestinal tract initially. Systemic effects are more prevalent in the internal organs and the hematopoietic system. Damage is not generally immediate and progresses over 24 hours, and exposure victims may experience a delay in overt symptoms.

One disclosed current embodiment of the invention concerns a CHL formulation that could provide significant protection from some of the systemic effects when administered prophylactically and will reduce the cellular damage of vesicating agents when given shortly after suspected exposure. A soft tablet formulation could be used both for systemic effects and chewed to provide a film of CHL in the moist areas of the oral mucosa and the gastrointestinal tract. These areas are particularly vulnerable and very high concentrations could be produced locally.

Protection for the lungs also is important. The lungs are a site of significant damage from mustard gas poisoning. Disclosed embodiments therefore also concern an inhaled dosage formulation.

Decontamination of mustard gas is achieved by either hydrolysis or oxidation. The major difficulty in mustard gas degradation is its low solubility in water. Ingesting chlorophyllin according to disclosed embodiments of the present invention will effectively render the toxin susceptible to attack by a nucleophilic agent. Chlorophyllin should promote the hydrolysis and/or oxidation of bis-(2-chloroethyl) sulfide before entering the blood stream.

Figure 6:
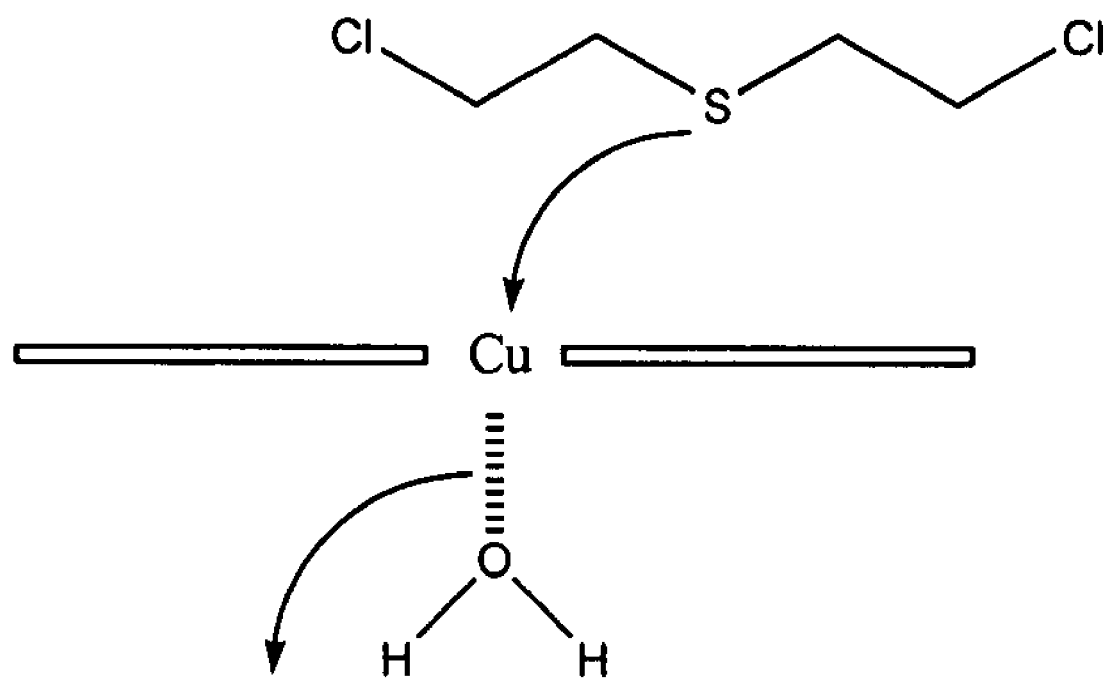
FIG. 6 schematically illustrates the interaction of Cu and sulfa mustard.
Figure 7:
FIG. 7 illustrates the Episulfonium ion.

As stated above, the copper of chlorophyllin has the ability to accept ligands. In the case of mustard gas, the sulfur atom is expected to be the electron pair donor, as illustrated in FIG. 6. Coordination increases the sulfur atom's propensity for oxidation. The major toxic agent of mustard gas is the readily formed episulfonium ion (FIG. 7) (Yang et al. 1988; Yang et al. 1986). Sulfur chelation by chlorophyllin inhibits the formation of the sulfonium ion and catalyzes the hydrolysis to the nontoxic hydrophilic bis-(2-hydroxyethyl) sulfide.

D. Other Uses

Low level chronic and high level acute exposure to natural and synthetic compounds with carcinogenic potential such as aflatoxin $B_1$ ($AFB_1$) or PAHs can produce significant toxicity and contributes to the risk of developing cancer. Primary prevention efforts seek to lower concentrations of these substances in the environment to reduce exposure. Treatments that include the use of pharmaceutical interventions are secondary measures, which can further reduce the systemic exposure to toxic and carcinogenic agents. Acute exposure to agents with toxic and/or carcinogenic potential are of great concern in the United States and to our military overseas because of risks associated with biological, biochemical and chemical terror threats. Exposure to PAHs through diesel fuels also contributes to the overall exposure of military and civilian personnel. JP-8 is now the single most common battlefield fuel for all U.S. Army and Air Force equipment, replacing gasoline altogether and currently replacing diesel. Its combustion produces emissions of CO, light volatile organic compounds, semi-volatile organic compounds with an emphasis on PAHs, particulate emissions, and nitrogen and sulfur oxides (Ritchie et al. 2003). Additionally, there is a growing awareness of the consequences of toxic release to our city populations from attacks or from natural catastrophes including fires or hurricanes. It is essential to develop safe, broadly effective medical countermeasures to treat high risk populations, including our military personnel, National Guard, and first responders, such as firefighters and police.

Natural and semi synthetic anti-carcinogens such as indole-3-carbinol and CHL, respectively, have been identified as bioactive molecules capable of reducing cancer risk. Encouraging results have been observed in animal models and in humans (Egner et al. 2001; Greenwald 1999; Kelloff et al. 2000). Preliminary clinical trials in China, where liver cancer rates are high (related to high dietary $AFB_1$ exposure and incidence of hepatitis infection) support the proposed application of CHL as a cancer chemopreventive agent (Dashwood 1997). Although there has not been a report on the systemic levels of $AFB_1$ and dibenzo(a,l)pyrene (DBP) in humans, one study investigated the effect of 100 mg CHL three times a day for 4 months on the disposition of $AFB_1$ in humans (Egner et al. 2001). Their results showed that CHL reduced the $AFB_1$ biomarker, $AFB_1$-DNA adducts, in the urine by 55% when compared to the placebo. Similar results have been seen with CHL and $AFB_1$ in trout and with CHL and DBP in trout (Breinholt et al. 1995; Reddy et al. 1999).

Mechanistic studies with several well characterized carcinogens such as DBP suggest that CHL acts as an "interceptor molecule" by forming high affinity complexes (Breinholt et al. 1995; Hartman & Shankel 1990). CHL is known to form tight molecular complexes with molecules such as DBP and $AFB_1$ with an apparent Kd of 1.59 µM and 1.4 µM, respectively, (Breinholt et al. 1995; Reddy et al. 1999). It has been proposed that these carcinogen-CHL complexes could impede the intestinal absorption and lower the systemic dose of carcinogens leading to reduced tumor incidence (Breinholt et al. 1999; Sugiyama et al. 2002), and several studies support such a mechanism (Hayashi et al., 1999; Simonich et al., 2007). Short-term genotoxicity assays (in vitro and in vivo) with CHL have demonstrated potent protection against several classes of mutagens, including aflatoxin and PAHs, and heterocyclic amines (Dashwood 1998). Binding studies and measurements of efflux in the Caco-2 cells suggest that CHL acts as an "interceptor molecule" by binding with high affinity to these molecules (Mata et al. 2004). Other mechanisms that have been proposed for CHL and related structures are: (i) inactivation of cytochrome P450s (CYP) involved in the bioactivation of environmental carcinogens (Yun et al. 1995); (ii) antioxidant and radical scavenging effects; and, (iii) trapping of polycyclic mutagens causing enhanced degradation and inhibiting mutagenicity (Tachino et al. 1994). The China clinical trial with CHL did suggest that significant levels of one CHL derivative was absorbed in test subjects and systemic effects did play some role in vivo (Egner et al. 2000). These data suggest that a preparation of CHL, specifically formulated to complex with a variety of chemical and biological agents, may be capable of intercepting toxins and toxic chemicals systemically and greatly reducing risks associated with chronic or acute exposures. Our discovery of several new reactions with CB not known prior to this invention enable the use of metalloporphyrins, which include CHL, for use as broad spectrum medical interventions to acute poisonings.

Recent additions to the possible treatments for acute aflatoxin exposure include the use of processed calcium montmorillonite clay (NovaSil) in dogs and humans (Afriyie-Gyawu et al. 2005; Wang et al. 2005). These clays are effective at binding aflatoxin in the intestine, reducing systemic exposure and aflatoxicosis. Unlike CHL, which will bind a large number of toxins and chemical carcinogens, certain clays are more specific for toxins such as aflatoxin (Phillips 1999; Phillips et al. 1995). The limited use of clays is one consideration; however, a more important consideration is timing of response to acute $AFB_1$ exposure. In order to understand the opportunity for intervention with CHL following $AFB_1$ exposure and its advantages over other binders, it is essential to consider the absorption and excretion pharmacokinetics of this toxin.

E. Aflatoxin $B_1$ $AFB_1$ is referred by some to be a "mid-spectrum" chemical warfare agent. Unlike classical chemical weapons which are generally fast acting, highly toxic and often lethal, mid-spectrum weapons have both incapacitating effects on humans and long term consequences such as the development of cancer (Aas 2003). The primary means of exposure, however, has been through contaminated grains with human exposures recently reported in Kenya (Muture & Ogana 2005). While $AFB_1$ may not be the most formidable weapon in a terrorist or military arsenal, considerable effort was focused on developing AFB1 as a weapon in Iraq under Saddam Hussein (1996). Aflatoxin exposure is difficult to diagnose clinically following exposure. One plausible explanation for its use as a weapon is the long-term deleterious effects of exposure within a country's sub-populations (Aas 2003).

The absorption of aflatoxin B1 ($AFB_1$) in the intestine has not been measured in humans. However, studies in other species provide a basis for estimating the absorption of $AFB_1$ in the small intestine. The absorption of $AFB_1$ in the rat follows first-order kinetics with an absorption rate constant ($k_a$) measured in situ of 5.84+/−0.05 $hr^{-1}$ (Ramos & Hernandez 1996). These results are confirmed, in principle, by Cupid et al., who compared rat and human dose effects on albumin adduct formation in the plasma after a single oral dosage of $AFB_1$ (Cupid et al. 2004). In the rat study, at 6 hours post-dose, $AFB_1$-albumin adducts in plasma were found at concentrations that were proportional to the dose. Human subjects given $AFB_1$ in this same report had adduct concentrations that were similar to what would be predicted based on the rat dose/effect curve. The $AFB_1$-albumin adducts were the predominant species found in the plasma of both rats and humans following oral administration in this study (personal communication). Although the human subjects received only one dose, these data suggest a rapid first-order process similar to the rat. Assuming that the absorption rate in rat is similar to human, an approximation of the absorption half-life of $AFB_1$ would be: $t_{1/2}$=0.693/5.84 or 0.119 hr. Based on this half-life, an oral dose would be almost completely absorbed within the first hour following administration in a fasted subject. The rapid absorption of $AFB_1$ following oral ingestion is significant in cases where treatment is not immediate. In these cases, a systemically active interceptor molecule would have utility and could reduce the effects of aflatoxicosis. Non-systemic aflatoxin binders would not be expected to reduce systemic bioavailability if the ingestion preceded the time to treatment by more than 0.4 hours (approximately 4 half-lives).

Many studies have characterized the molecular dosimetry of $AFB_1$ as a measure of possible carcinogenic effects (Bailey et al. 1994; Gorelick 1990; Kensler et al. 1997; Wong & Hsieh 1980). These studies have primarily focused on the biological half-life of $AFB_1$. It is important to distinguish between biological half-life and terminal half-life when considering the residence time of a molecule in the body. The pharmacokinetics of $AFB_1$ have been studied in multiple species including Rhesus monkey by Wong and Hsieh (Wong & Hsieh 1980). In this study of IV administration of $AFB_1$ in monkeys (10% of the LD50 or 0.3 mg/Kg verses 31.2 ng or approximately 0.45 ng/Kg), the terminal excretion pattern suggests that $AFB_1$ is excreted primarily though the kidney within the first 24 hours with 40% of the dose being eliminated as either unbound (~30%) or chloroform extractable from the urine (~10%). It is during the first 24 hours that a systemically available $AFB_1$ interceptor molecule would be most effective. Fecal excretion constitutes ~4% of the excreted dose in the first 24 hours. However, between 24 and 48 hours elimination in the feces accounts for 20% of the administered dose, followed by another ~6% between 48 and 72 hours and ~3% of administered dose between 72 and 100 hours. In the monkey, 100 hours following administration of $AFB_1$, 13.6% of the dose remained in the liver with 5.8% remaining in the plasma, suggesting that a significant fraction of the dose has a long residence time. Although the China study demonstrates the increased excretion of $AFB_1$ in subjects chronically exposed to dietary $AFB_1$, it is not known if an interceptor molecule such as CHL can access these sites of $AFB_1$ sequestration (Egner et al. 2003).

After 100 hours, in the monkey total excreta were found to be 73.1% of administered dose (Wong & Hsieh 1980). The results of this study demonstrate a mixed excretion pattern for AFB1 with renal excretion being the predominant form in the first 24 hours followed by biliary excretion. Further, this data suggests that, in the monkey, the terminal half-life ($t_{1/2}\beta$) from all routes of excretion is approximately 24 hours following IV administration. Data from mice and rats in this same study suggest that, although fecal excretion was predominant rather than renal excretion following oral dosing, the terminal half-life was similar to monkey when all routes of excretion were considered.

Following a single oral administration of aflatoxin in sheep approximately 90% of the total dose is excreted in the first 48 hours after treatment (Clarke 1981). This suggests that the $t_{1/2}$ in sheep is approximately 24 hours, which is similar to monkey, rat and mouse. These few kinetic studies provide an indication that the kinetics of $AFB_1$ will provide a window of opportunity to reduce the systemic dose of toxin by administration of an $AFB_1$ interceptor molecule.

In summary, based on the available information in humans and other species, the complete absorption $AFB_1$ in a fasted individual is expected to be rapid and on the order of 0.5-1.0 hours. This will limit the opportunity for a binder that does not have systemic bioavailability. Following the absorption phase, a conservative estimate is that the terminal half-life of $AFB_1$ will be less than 24 hours, with nearly 100% of the dose excreted within 4 days. This kinetic profile suggests that treatment with CHL is reasonable for the treatment of acute $AFB_1$ exposure for the first 24-48 hours.

F. PAH Exposure

Particulate and chemical inhalation, including PAH exposure, as a result of terrorist acts were well documented following the World Trade Center bombings. During the first 24-48 hours burning jet fuel was a predominant form of pollution and was partially responsible for the significant short term health and environmental consequences reported (Landrigan et al. 2004). First responders were especially vulnerable due to their proximity to the sources of these toxins. Follow-up medical evaluation of 10,116 firefighters was conducted over the 6 months after the attack with 38% having high serum levels of polychlorinated biphenyls and PAH (Kelly et al. 2002). Of those studied, 332 firefighters also suffered from a persistent cough accompanied by other respiratory symptoms so severe as to require at least 4 weeks' leave of absence, termed "World Trade Center cough" (Chen & Thurston 2002). Prevalence of WTC cough was related to intensity of smoke exposure, and occurred in 8% of firefighters with a high level of exposure, 3% with moderate exposure, and in 1% with low-level exposure (Landrigan et al. 2004). Other symptoms included bronchial hyperreactivity, eosinophilic pneumonia, and increases in neutrophil and eosinophil counts in sputum samples (Beckett 2002; Prezant et al. 2002; Rom et al. 2002). These abnormalities were positively correlated with exposure to dust and combustion products and levels of PAHs in the bodies of firefighters (Edelman et al. 2003).

CHL is known to complex with a number of PAHs in vitro and has demonstrated efficacy as a cancer chemopreventive agent in vivo. Chemicals, metal ions and various biologics that either complex with or are chelated by CHL are listed in Table 1 along with proposed mechanism of action and their respective studies. The chemicals known to complex with CHL share the general characteristic of containing cyclic structure, and often are planar.

The utility of CHL as a cancer chemopreventive agent is well characterized (Dashwood 1997). In human studies of PAH exposure chlorophyll has been shown to significantly reduce the body burden of long-lived species of halogenated hydrocarbons (Nagayama et al. 2005). However, the broad applicability of CHL as a medical intervention for acute exposure to PAH's following occupational exposure, chemical release from a terror act or catastrophe has not been sufficiently studied.

In order to understand the magnitude of the problem of PAH exposure within the military and the possible utility of CHL as a safe effective medical countermeasure, it is important to understand the prevalence of contact with commonly used fuels. Occupational exposure to PAH through JP-8 is high among military and civilian personnel with more than 2 million people per year (over 1 million in the United States) exposed to jet propulsion fuel-8 (JP-8), JP-8+100 or JP-5, or to the civil aviation equivalents Jet A or Jet A-1. Approximately 60 billion gallons of these kerosene-based jet fuels are annually consumed worldwide (26 billion gallons in the United States), including over 5 billion gallons of JP-8 by the militaries of the United States and other NATO countries. JP-8, for example, represents the largest single chemical exposure in the U.S. military (2.53 billion gallons in 2000), while Jet A and A-1 are among the most common sources of nonmilitary occupational chemical exposure (Ritchie et al. 2003). These exposures may contribute to the significant reduction of neurocognitive function observed in military personnel exposed to these fuels on the flight deck (Tu et al. 2004). Also, increased sensitivity to JP-8 has been demonstrated among Gulf War veterans exhibiting polysymptomatic conditions (Gulf War syndrome) (Bell et al. 2005).

It is difficult to predict the effects of CHL intervention on the overall toxic response to JP-8 because CHL would not be expected to complex with all the components found in JP-8 or its combustion products. However, because a number of the components and combustion products are PAHs, there is a high probability that CHL would have a significant impact and would be expected to reduce cancer risk associated with systemic exposure to carcinogens found in JP-8 and related fuels. Very little research has been reported on CHL formulations that provide increased bioavailability in humans. Recently, chlorine (E4) ethyl ester, present in relatively high levels in Derifil™, was found in the serum of patients enrolled in the China trial (Egner et al. 2000). The recent discovery that CHL is bioavailable in humans is not surprising since it has long been known that preparations of CHL will impart a green coloration on almost all organs of the body in other species (Kephart 1955). This "rediscovery" of an important property of CHL allows for speculation that an enhanced formulation of CHL could be used as a medical countermeasure to reduce PAH exposure.

G. Metal Chelation and Radioisotopes

Early studies suggest that chlorophyllin is an effective chelator for metals and may have utility as a medical countermeasure for exposure to toxic metals including those isotopes that contribute to radiation sickness (Kasugai 1964). chlorophyllin has demonstrated efficacy as an agent capable of reducing clastogenicity resulting from the ingestion of three potent metallic clastogens (cesium chloride, mercuric chloride and cobalt chloride) in bone marrow cells of mice in vivo. However, prophylactic administration of chlorophyllin 2 hours prior to metal ion administration was not protective, suggesting that the anti-clastogenic effects may be due to chelation in the intestine rather than the effects of systemic chlorophyllin (Ghosh et al. 1991). Other clastogens such as chromium (VI) oxide also appear to be targets for chlorophyllin chelation (Sarkar et al. 1993).

III. Safety

Water soluble chlorophyllin copper complex has the central magnesium atom replaced by a copper atom and its methyl and phytyl ester groups replaced by sodium and potassium. Any toxic effects are, therefore, in part, due to free ionizable copper present in the complex. Harrison et al. published a definitive work on the toxicology of potassium sodium chlorophyllin copper complex finding it (4 percent total Cu, 0.25 percent. ionic Cu) in concentrations above 0.1 percent of the diet appears as chlorophyllin and Cu ions in the plasma. Unlike other forms of copper that show significant dose and time dependent accumulation of copper in tissues (liver, kidney, spleen), potassium sodium copper chlorophyllin was only modestly increased at 1.0% compared to 3% in the diet regardless of the number of weeks of exposure (10, 52 or 104 weeks). This suggests a rather short tissue half-life for CHL, which will be useful in managing of Joint Services personnel that would receive treatment. No copper storage occurred in liver, kidney or spleen of rats at dietary levels of 0.1 percent, or 1 percent of sodium and potassium chlorophyllin copper complex. There was no effect on iron storage at these levels. Guinea-pigs fed 0.5 percent or rats fed 3 percent. of the complex in their diet showed no evidence of scurvy (Harrison et al. 1954).

Acute toxicity is not an anticipated problem and CHL products are considered Generally Regarded as Safe (GRAS). They have been extensively studied in multiple animal species and are commercially available in over-the-counter formulations. A summary of acute toxicity is presented below and in Table 2 (WHO 1969). Although the proposed product is a well-defined formulation and does not contain mixtures of chlorins, we expect that our product will have a similar safety profile compared to commercially available preparations.

There are a growing number of studies that demonstrate the safety of relatively high doses of CHL. Six mice were given 2500 mg/kg body-weight sodium CHL orally for 7 days without any ill effects (Worden et al. 1955). Five male and 4 female rats were fed a diet containing 15 percent sodium potassium chlorophyllin for 10 days without any adverse effects except weight loss related to food refusal (Harrison et al. 1954). Two guinea-pigs, 2 rabbits, 2 cats and 1 dog were given CHL 1000 mg/kg body-weight, orally daily for 7 days without any adverse effects (Worden et al. 1955).

Chronic dosing regimens with CHL include studies in rats in which thirty animals received oral doses of 2000 mg/kg body-weight CHL for 18 weeks without any adverse effects (Worden et al. 1955). Offsprings of 6 female rats fed 1 percent. of sodium potassium CHL for 19 weeks exhibited locomotory difficulties and skeletal muscle defects (Reber & Willigan 1954). Five female guinea-pigs received 0.5 percent sodium potassium chlorophyllin in their drinking water for 11 weeks without ill effects or pathological change. There was no evidence of scurvy (Harrison et al., 1954). Sixty-day-old chickens received orally 70 mg/kg body-weight CHL for 6 weeks and 8-year-old fowls received 500 mg/kg body-weight for 3 weeks without gross adverse effects. The yolk of all eggs laid was colored an intense green (Worden et al. 1955).

Long-term studies in rats include groups of 40 animals fed diets containing 0, 0.1, 1.0 and 3 percent of sodium potassium copper chlorophyllin (4-5 percent total Cu, 0.25 percent ionic Cu) over their life span. Growth rate, feed efficiency, hematology and urinalysis were comparable to the controls. Reproduction showed no impairment of conception. No gross or histopathological changes were attributable to the sodium potassium copper chlorophyllin were seen. There was no evidence of Cu toxicity or deposition in liver, kidney or spleen. The copper in these complexes is firmly bound and although increased plasma levels of copper have been reported there is no significant tissue storage nor is there any evidence of destruction of ascorbic acid (Harrison et al. 1954).

Current levels that have been determined to cause no toxicological effect in the rat are 3 percent (=30 000 ppm) in the diet equivalent to 1500 mg/kg body-weight per day. Estimates of acceptable daily intake of CHL for man are 0-15 mg/kg body-weight. When calculating the dose in a 70 kg human we would thus estimate a maximum dose of 1.05 gm per day as an upper limit to the recommended daily intake of CHL. The recommended dosage for the over-the-counter medication Derifil is 100 mg tablet BID or a total or 200 mg per day.

TABLE 2

Acute Toxicities of chlorophyllins

| Compound | Animal | Route | LD50 mg/kg body-Weight | Reference |
|---|---|---|---|---|
| Potassium sodim chlorophyllin | mouse | Oral | 7000 | (Harrison et al. 1954) |
| Copper complex chlorophyllin | mouse | i.p. | 190 | (Harrison et al. 1954) |
| Sodium chlorophyllin copper complex | mouse | i.v. | >400 | (Worden et al. 1955) |
| | | i.m. | >500 | |
| | | i.p. | >1000 | |
| | rat | i.v. | >250 | |
| | | i.m. | >250 | |
| | | i.p. | >1000 | |
| | rabbit | i.v. | >200 | |
| | | i.m. | >60 | |
| | | i.p. | >500 | |
| | cat | i.p. | >60 | |
| | dog | i.v. | >200 | |
| | | i.m. | >50 | |
| | | i.p. | >200 | |
| | pig | i.v. | >10 | |
| | | i.m. | >20 | |

Figure 8:
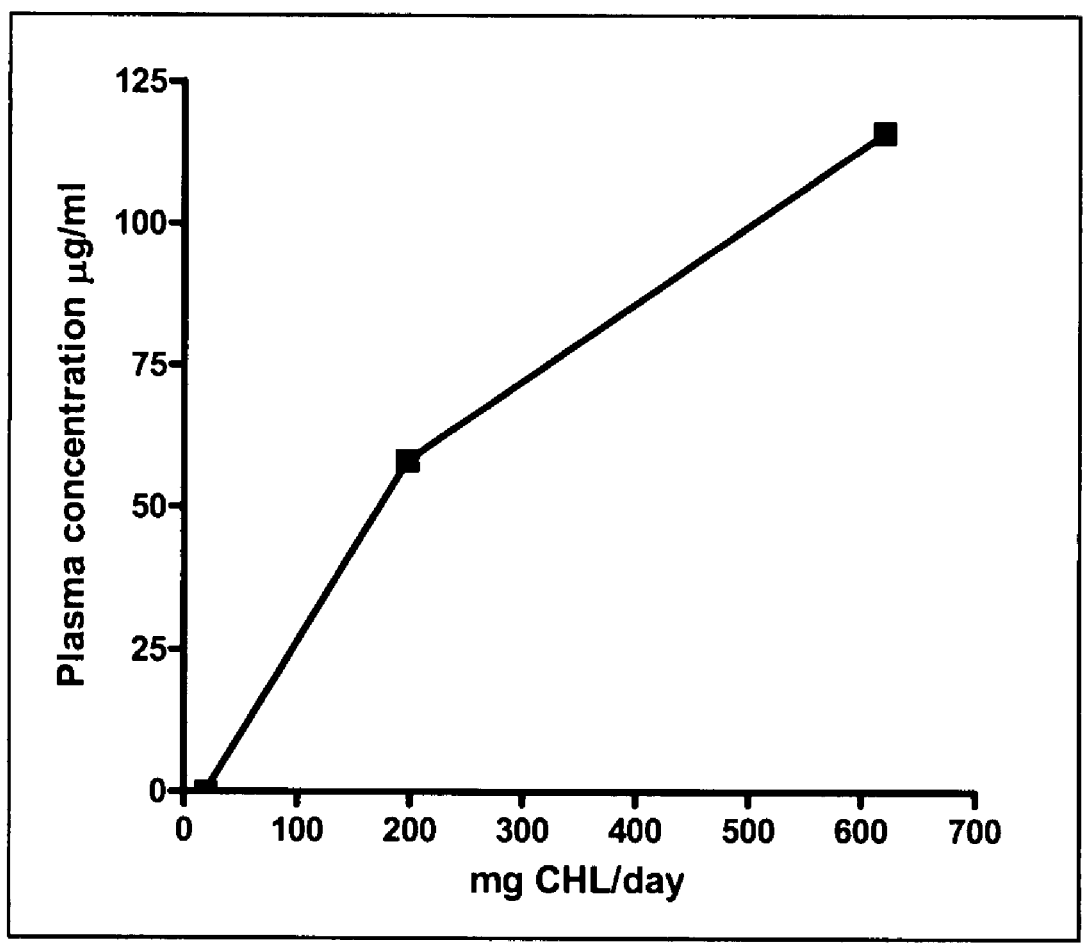
FIG. 8 is a graph of estimated plasma concentration (µg/ml) versus milligrams of CHL/day based on early work with CHL by Harrison et al., 1954.

Early studies with CHL included chronic dosing of rats. Re evaluation of some of the published data suggests that plasma concentrations reach steady state based on the daily intake of CHL. As can be seen in FIG. 8, the steady state plasma concentration is less than proportional to the daily dose. This suggests a CHL terminal half-life that is less than 24 hours. Because we are proposing a dosage formulation suitable for acute exposure, a half-life of less than 24 hours will make dose scheduling convenient and will allow levels to decrease to very low levels in a short amount of time. This will help to avoid photosensitivity that can accompany CHL administration.

IV. Extracting Chlorophyll

Figure 9:
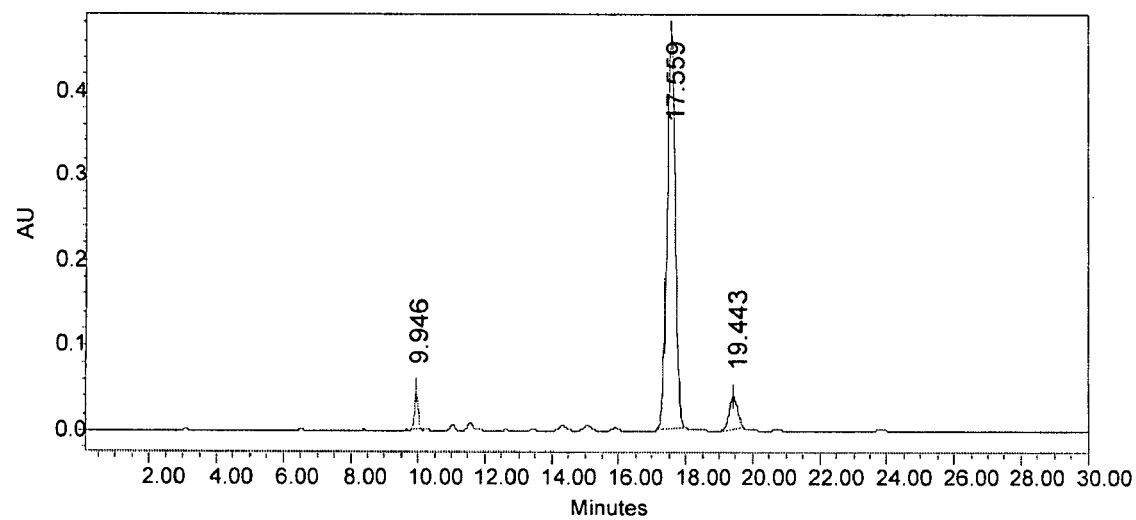
FIG. 9 is a HPLC trace of chlorophyll a, a' following extraction from a *Spirulina* organism, with purity estimated to be 96.27% with some residual carotenoids.

Certain disclosed embodiments concern extracting chlorophyll from suitable sources, such as plant and algae, such as blue-green algae, to yield a raw material that is highly enriched for chlorophyll a and a'. Chlorophylls are the precursor to chlorophyllin. The disclosed embodiments provide a starting material for conversion to chlorophyllin that is 94-98% chlorophyll a or a'. Other methods use a series of extractions that allow chlorophyll to be processed from crude sources such as alfalfa or spinach. However, much of the processing is required to reduce the amount of extraneous material that is co-extracted along with the mixtures of chlorophylls that are found in these sources. Before any chromatographic purification techniques are employed, the original source (including, but not limited to, plants and algae) are comminuted and washed with at least one solvent, typically solvents, with a working embodiment using petroleum ether and methanol/petroleum ether (a form of liquid/solid extraction). This solution is then further refined by washing with either an organic or aqueous phase (a form of liquid/liquid washing) producing a complex mixture as seen in FIG. 9. Disclosed embodiments of the process produce a fraction of this mixture having a substantially higher yield of chlorophyll and predominantly chlorophyll a than presently existing commercial sources. The preferred starting material for the production of a highly pure metalloporphyrin is *Spirulina pacifica*.

Embodiments of a method for extracting chlorophyll from a suitable source using counter current chromatography to produce a fraction substantially enriched in chlorophyll are disclosed in U.S. provisional patent application No. 60/817, 978, which is incorporated herein by reference. The '978 patent application illustrates the process with reference to working embodiments concerning extracting materials from freeze dried spinach. Briefly, a working embodiment of this process was accomplished as described in the working examples.

V. Derivatives of Chlorophyll

After isolation of substantially pure chlorophyll, derivatives of the chlorophyll may be prepared, either by conventional synthetic routes, or alone or in combination with enzymatic changes. Examples of chlorophyll derivatives, without limitation, are listed in U.S. Pat. No. 5,650,292, which is incorporated herein by reference.

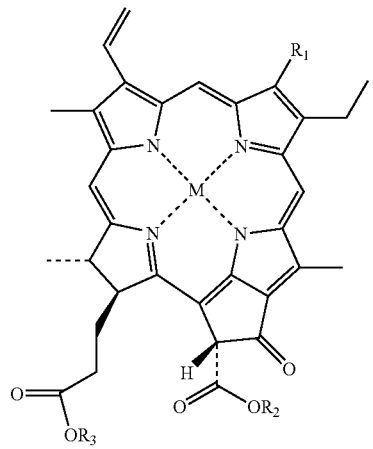

Formula 1

With reference to Formula 1, such compounds include, but are not limited to formulas where M is typically a metal ion with a charge of +2 selected from beryllium, magnesium, calcium, strontium, barium, chromium, manganese, iron, cobalt, nickel, copper, zinc, molybdenum, technetium, ruthenium, rhodium, palladium, cadmium, tungsten, rhenium, osmium, iridium, platinum, and mercury. Metal cations with +1 or +3 charges also could be used, though this would produce a complex with either a −1 charge (if the metal has a charge of +1) or +1 (if the metal has a charge of +3). A person of ordinary skill in the art would be able to balance any such overall charge with an appropriate counter ion or ions. $R_1$ typically is an aliphatic moiety, such as a hydrocarbon or hydrocarbon chain, lower (fewer than 10 carbon atoms) alkyl groups, such as methyl and ethyl, or a carbonyl bearing moiety, such as an aldehyde, ketone or ester. $R_2$-$R_4$ independently are aliphatic chains having 20 carbon atoms or fewer, particularly alkyl groups, and even more particularly alkyl groups having 20 or fewer carbon atoms in the chain, including lower (fewer than 10 carbon atoms) alkyl groups. The hydrocarbon chain may be saturated or unsaturated; interrupted by heteroatoms such as N, O and/or S; contain saturated or unsaturated cyclic structures with or without heteroatoms; or contain functional groups including by way of example and without limitation, alcohols, amines, aldehydes, carboxylic acids, esters, ethers, epoxides, ketones, thiols, sulfides, phosphines and phosphates. $R_2$-$R_4$ also may be biologic moieties. For example, $R_2$-$R_4$ may comprise a carbohydrate, lipid, steroid, amino acid, peptide, protein, nucleoside, nucleotide, oligonucleotide, oligonucleoside, or nucleic acid (including DNA and RNA). $R_2$-$R_4$ also can be positively charged species, such as metal ions with a charge of +1 selected from lithium, sodium, potassium, cesium, chromium, manganese, iron, cobalt, nickel, copper, zinc, molybdenum, technetium, ruthenium, rhodium, palladium, silver, cadmium, tungsten, rhenium, osmium, iridium, platinum, gold, and mercury; or a non-metallic singly charged cation such as ammonium. A metal cation with a charge of +2 or +3 also could be used, though it would produce a complex with an overall charge. A person of ordinary skill in the art would be able to balance such charge with an appropriate counter ion or ions.

VI. Conversion of Chlorophyll to Cholorphyllin

Substantially pure chlorophyll may be converted to a chlorophyllin. Examples of metal chlorophyllins, without limitation, are listed in U.S. Pat. No. 5,770,404, which is incorporated herein by reference. First, the ester groups of chlorophyll a, a', b or b' may be saponified to provide carboxylic acid functional groups or the conjugate base in place of these esters. Saponification also may ring open one or more of the substitutent rings. Optionally, acidification by a suitable acid (including, but not limited to, hydrochloric acid or trifluoroacetic acid) neutralizes the molecule, creating preferential partition of the compound into an organic phase. Subsequent addition of a metal cation, preferably a metal cation with a +2 charge selected from the group, beryllium, calcium, strontium, barium, chromium, manganese, iron, cobalt, nickel, copper, zinc, molybdenum, technetium, ruthenium, rhodium, palladium, cadmium, tungsten, rhenium, osmium, iridium, platinum, and mercury, displaces magnesium from the central ring in a transmetallation reaction. Metal cations with +1 or +3 charges also could be used, though it would produce a complex with an overall charge that a person of skill in the art would be able to balance with an appropriate counter ion or ions. Finally, the acidic groups may be neutralized with a suitable base (including, but not limited to, sodium, potassium or ammonium hydroxide) to provide a water soluble form of the cholorphyllin.

U.S. Pat. No. 5,770,404 also provides examples of synthetic derivatives of chlorophyllins. In lieu of neutralization, carboxylic acid functional groups may be converted to various esters by standard esterification reactions, typically after transmetallation.

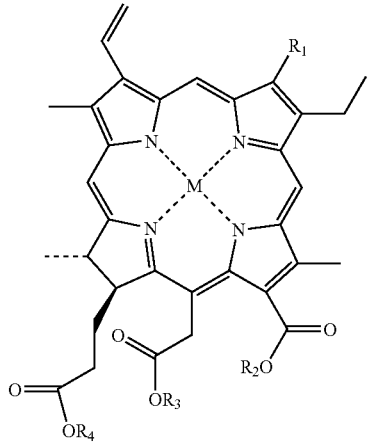

Formula 2

With reference to Formula 2, such compounds include, but are not limited to those where M is typically a metal ion with a charge of +2 selected from beryllium, magnesium, calcium, strontium, barium, chromium, manganese, iron, cobalt, nickel, copper, zinc, molybdenum, technetium, ruthenium, rhodium, palladium, cadmium, tungsten, rhenium, osmium, iridium, platinum, and mercury. Metal cations with +1 or +3 charges also could be used, though this would produce a complex with either a −1 charge (if the metal has a charge of +1) or +1 (if the metal has a charge of +3). A person of ordinary skill in the art would be able to balance any such overall charge with an appropriate counter ion or ions. $R_1$ typically is an aliphatic moiety, such as a hydrocarbon or hydrocarbon chain, lower (fewer than 10 carbon atoms) alkyl groups, such as methyl and ethyl, or a carbonyl bearing moiety, such as an aldehyde, ketone or ester. $R_2$-$R_4$ independently are aliphatic chains having 20 carbon atoms or fewer, particularly alkyl groups, and even more particularly alkyl groups having 20 or fewer carbon atoms in the chain, including lower (fewer than 10 carbon atoms) alkyl groups. The hydrocarbon chain may be saturated or unsaturated; interrupted by heteroatoms such as N, O and/or S; contain saturated or unsaturated cyclic structures with or without heteroatoms; or contain functional groups including by way of example and without limitation, alcohols, amines, aldehydes, carboxylic acids, esters, ethers, epoxides, ketones, thiols, sulfides, phosphines and phosphates. $R_2$-$R_4$ also may be biologic moieties. For example, $R_2$-$R_4$ may comprise a carbohydrate, lipid, steroid, amino acid, peptide, protein, nucleoside, nucleotide, oligonucleotide, oligonucleoside, or nucleic acid (including DNA and RNA). $R_2$-$R_4$ also can be positively charged species, such as metal ions with a charge of +1 selected from lithium, sodium, potassium, cesium, chromium, manganese, iron, cobalt, nickel, copper, zinc, molybdenum, technetium, ruthenium, rhodium, palladium, silver, cadmium, tungsten, rhenium, osmium, iridium, platinum, gold, and mercury; or a non-metallic singly charged cation such as ammonium. A metal cation with a charge of +2 or +3 also could be used, though it would produce a complex with an overall charge. A person of ordinary skill in the art would be able to balance such charge with an appropriate counter ion or ions.

VII. Working Examples

The following examples are provided to illustrate certain features or working embodiments of the disclosed invention. A person of ordinary skill in the art will appreciate that the scope of the invention is not limited to those features exemplified by these examples.

EXAMPLE 1

Chlorophyll and its derivatives are light sensitive. As a result, the process is advantageously conducted in dim or no light conditions. Fresh spinach leaves were first washed with water, and then freeze-dried and refrigerated until use. A thirty gram sample of dried spinach leaves (corresponding to about 450 grams of fresh spinach) was washed twice in a blender with 500 milliliters of petroleum ether (b.p. 30-60° C.) to remove a portion of the carotenoids and then extracted twice using 400 milliliters of methanol/petroleum ether (3:1v/v). The mixture was filtered using a fritted funnel to separate spinach particles from solvents. Combined extracts were transferred to a separatory funnel and washed with 250 milliliters of saturated sodium chloride to pull the methanol into the aqueous layer. The organic petroleum ether layer contained the dark chlorophyll pigment. The aqueous layer was extracted with 200 milliliters of petroleum ether. Petroleum ether layers were combined and washed with 100 milliliters of saturated sodium chloride. The final extract was filtered and evaporated in vacuo. The residue was dissolved with 50 milliliters of acetone and left to precipitate impurities. The acetone fraction was filtered onto a clean fitted funnel and evaporated in vacuo.

Extracted material was then further purified using counter current chromatography (CCC). CCC was performed using an Ito multilayer-coil separator-extractor produced by P.C. Potomac. Maryland. The radius of the column orbit was 10.2 cm and the coil was 18 cm in diameter and 5 cm thick, with windings from a 10.2-cm hub ($\beta$=0.5) to the coil outer diameter ($\beta$=0.85). The multilayer coil consisted of a single piece of 2.7 mm I.D. PTFE tubing with a total capacity of 400 mL. Revolution speed was adjustable from 1 to 1,000 rpm using a speed controller from Bodine Electric Co., Chicago, Ill.

The stationary phase (heptane for chlorophyll a and ethanol for chlorophyll b) was loaded into the inlet of the coil in the absence of rotation, followed by crude dissolved product. Rotation (forward/clockwise for chlorophyll a and reverse/counter clockwise for chlorophyll b) was then started at a revolution speed of 700 rpm and the mobile phase (ethanol for chlorophyll a and heptane for chlorophyll b) was introduced into the column at a flow rate of 5 milliliters/minute. Chromatographic runs were monitored at 440 nanometers using a V4® Absorbance Detector, from Isco, Inc., Lincoln, Nebr. Purity analysis was conducted by HPLC using an Alltima C18 column at 35° C. and a flow rate of 1 milliliter/minute. For separating chlorophylls, eluent A was methanol/0.5M ammonium acetate (4:1, v/v) and eluent B was methanol/acetone (9:1, v/v). Product amounts were quantified using a DU-70 UV-vis spectrophotometer, using corrected equations, per Porra et al., *Biochmicica et Biophysica Acta*, Bioenergetics, 975 (1989), 384.

For isolating chlorophylls a and b, a lower aqueous phase was used for the mobile phase during CCC for a separation run requiring about 2 hours and 30 minutes. Chlorophylls (b, b', a and a') were isolated, and an exceptionally good chlorophyll a separation was obtained. A tail-to-head elution was used to isolate pure chlorophyll b. Product structure was confirmed by $^1$H-NMR and mass spectrometry. The $^1$H NMR spectra of the chlorophylls were recorded on a Bruker 400 MHz spectrometer with deuterated acetone as the solvent ($\delta$2.05). MS analysis was performed on a JEOL MSRoute (JMH-600) magnetic sector mass spectrometer. A FAB positive ion mass spectrum was recorded using Xenon and the sample matrix was 3-nitrobenzylalcohol.

Figure 14:
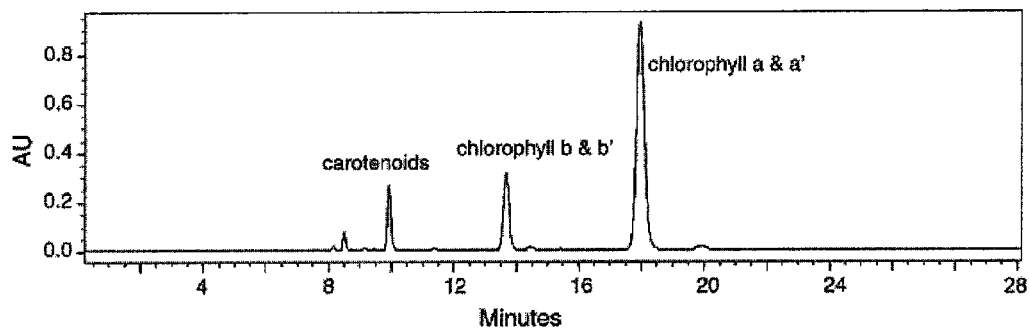
FIG. 14 is an HPLC chromatogram of a crude spinach extract.
Figure 15:
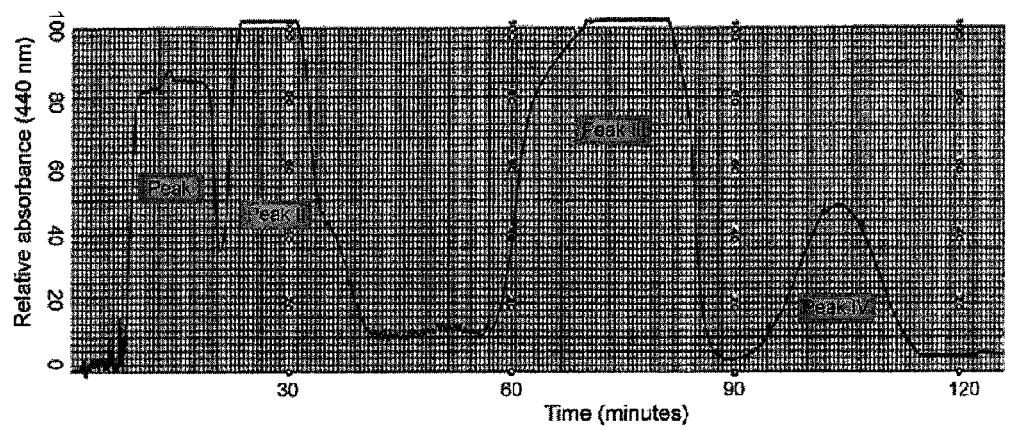
FIG. 15 is a chromatogram (monitored at 440 nm) illustrating the countercurrent chromatography (CCC) separation of a spinach crude extract.
Figure 16A:
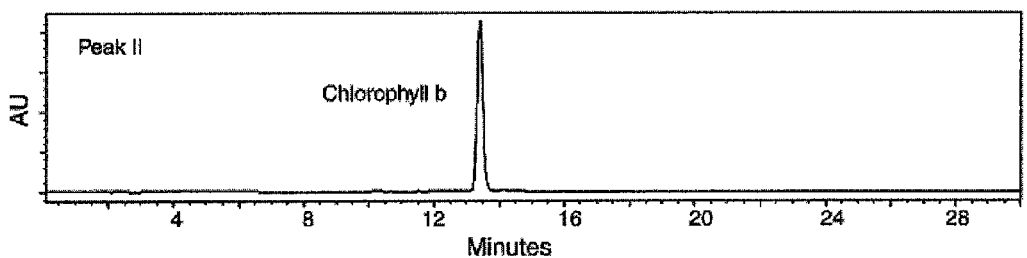
FIG. 16A is an HPLC chromatogram of a chlorophyll b fraction obtained by CCC separation of a spinach crude extract.
Figure 16B:
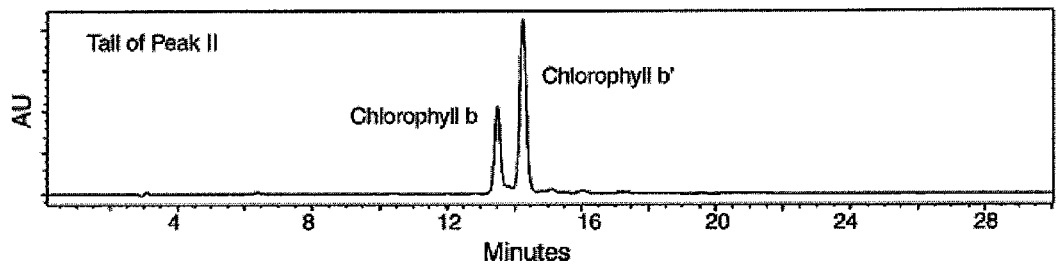
FIG. 16B is an HPLC chromatogram of a chlorophyll b/b' fraction obtained by CCC separation of a spinach crude extract.
Figure 16C:
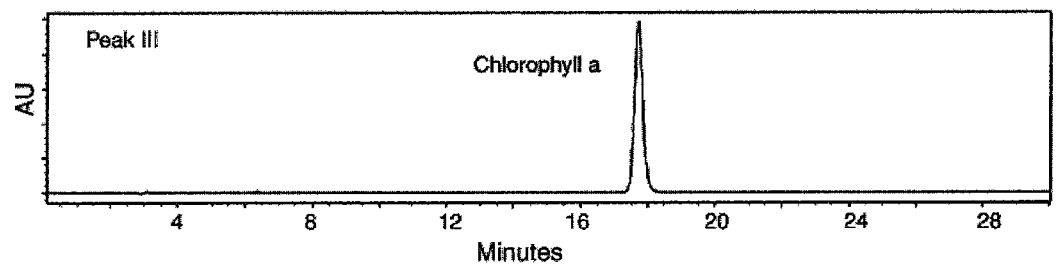
FIG. 16C is HPLC chromatogram of a chlorophyll a fraction obtained by CCC separation of a spinach crude extract.
Figure 16D:
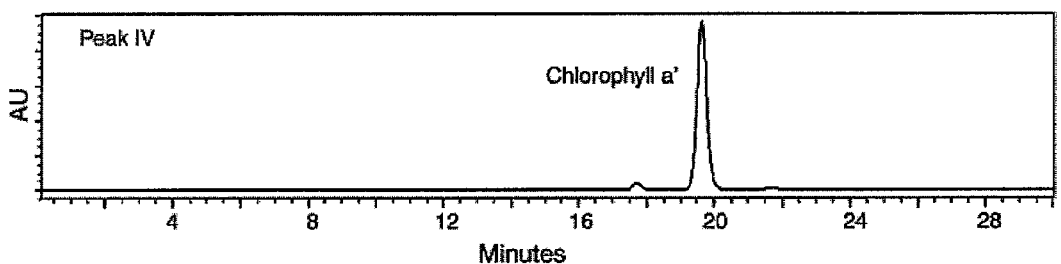
FIG. 16D is an HPLC chromatogram of a chlorophyll a' fraction obtained by CCC separation of a spinach crude extract.
Figure 17:
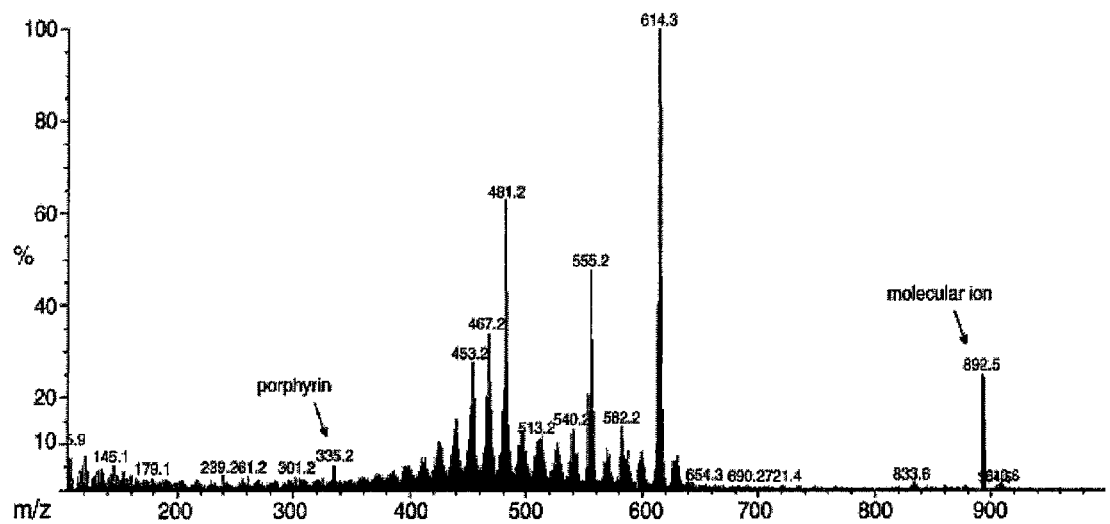
FIG. 17 is a mass spectrum of the chlorophyll a fraction of FIG. 16C.
Figure 18:
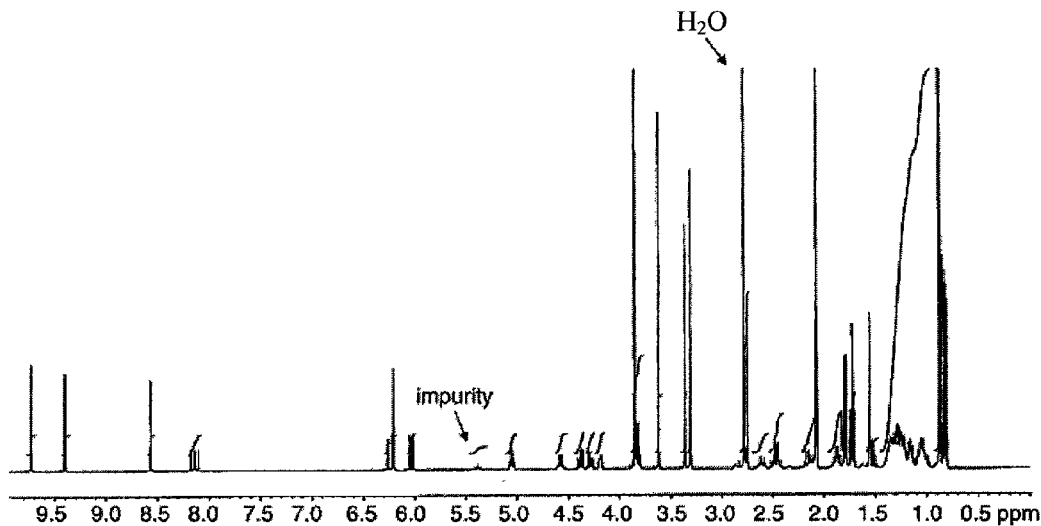
FIG. 18 is an NMR spectrum of the chlorophyll a fraction of FIG. 16C.

An HPLC chromatogram of the crude extract is shown in FIG. 14. The HPLC showed good separation of chlorophylls a and b and their epimers a' and b'. The chromatogram of the CCC separation of the crude extract from spinach (heptanes as the stationary phase) is given in FIG. 15 and shows the separation of carotenoids (peak I), chlorophyll b/b' (peak II), chlorophyll a (peak III) and chlorophyll a' (peak IV). The respective HPLC chromatograms of the isolated chlorophylls are shown in FIGS. 16A-16D. The chromatographic behavior of the isolated chlorophylls was identical with authentic standards on reverse-phase HPLC. The exact mass for chlorophyll a (892.5317 AMU) for the molecular ion was within 4 ppm of the theoretical value (892.5353 AMU). Furthermore, a low resolution, wide mass range FAB-MS of chlorophyll a showed the significant mass peaks at 481 (55%), 555 (40%), 614 (100%), and 893 (20%). All the peaks had complex isotope patterns implying the presence of magnesium (FIG. 17). The $^1$H-NMR spectrum of the isolated chlorophyll a was determined in deuterated acetone. The spectrum was characteristic of chlorophyll a (FIG. 17). A minor impurity was noticed at $\delta$5.40 consisting of 0.35 protons upon integration, and the only other extra peaks were the NMR solvent ($\delta$2.05) and the two signals due to H$_2$O and HOD ($\delta$2.78 and 2.75). The proton chemical shifts of the isolated chlorophyll a were in agreement with published spectra. Purity was estimated to be greater than 95% (100% by UV-VIS) compared to chlorophyll a standards obtained from Sigma Chemical Co., which routinely are between 90-92% pure. Thirty grams of freeze-dried spinach produced 300 milligrams of chlorophyll a and 100 milligrams of chlorophyll b.

EXAMPLE 2

Sodium copper chlorophyllin, Aflatoxin B$_1$ (AFB$_1$), tricaprylin, and triethylene glycol were obtained from Sigma Chemical Co. (St. Louis, Mo.). [$^3$H]-Aflatoxin B$_1$ (21.8 Ci/mmole) was obtained from Moravek Biochemicals, Inc. (Brea, Calif.). The purity and concentration of AFB$_1$ was confirmed by absorbance in ethanol at 362 nm ($\epsilon_{362}$=2.18× 10$^4$ M$^{-1}$). The chlorin content of CHL was based on the manufacturer's assay of 4.5% copper and assertion that all copper was present as copper-chlorins (Lot #14H0602, 51.3% Cu-chlorin content, additional material is water soluble Na salts). Chlorophyll was prepared as described below.

Organic spinach was washed with cold water, freeze-dried, washed twice with petroleum ether (b.p. 30-60° C.) and the solids extracted twice using methanol/petroleum ether (3:1, v/v). The combined extracts were washed with saturated sodium chloride, filtered and evaporated in vacuo (T<30° C.). This crude Chl extract (90% pure by HPLC) was further purified by counter current chromatography (CCC) using an Ito multilayer-coil separator-extractor (P.C., Potomac, Md.). Analyses of CCC fractions were performed by HPLC, MS and $^1$H-NMR. A minor impurity was detected at $\delta$ 5.40 consisting of 0.35 protons upon integration, and the only extra peaks were the NMR solvent ($\delta$ 2.05) and the two signals due to H$_2$O and HOD ($\delta$ 2.78 and 2.75). Purity was estimated to be >95%, compared to Chl-a standards (Sigma Chemical Co.), which were 90~92% pure based on spectroscopic measurements. Thirty grams of freeze dried spinach yielded 225 mg of Chl-a and 75 mg of Chl-b for a total yield of 300 mg Chl, or 1% by dry weight. Chl preparations used in all experiments were a recombined 3:1 mixture of Chl-a:Chl-b.

EXAMPLE 3

This example concerns the action of sodium copper chlorophyllin in reversing enzymatic inhibition of acetylcholinesterase.

The concentration of purified human recombinant acetylcholinesterase in a phosphate buffer was set at 0.01 µM and the substrate (acetylcholine) concentration was set at the $K_M$ of 100 nM. A concentration of 0.01 µM DFP was used to provide approximately 50% reduction in acetylcholinesterase activity. For the CHL treatment 10 µM CHL was incubated with DFP for 2 hours prior to addition of substrate and enzyme at 25° C. The 10 µM CHL concentration was chosen because this concentration can be achieved in the plasma following an oral dose. Substrate conversion rate increased by approximately 50% when CHL was present compared to the DFP inhibited enzyme. See FIG. 4. This example demonstrates the acetylcholinesterase reactivation potential of CHL.

EXAMPLE 4

This example concerns the effect of CHL on the ability of DFP to inhibit acetylcholinesterase.

Figure 5:
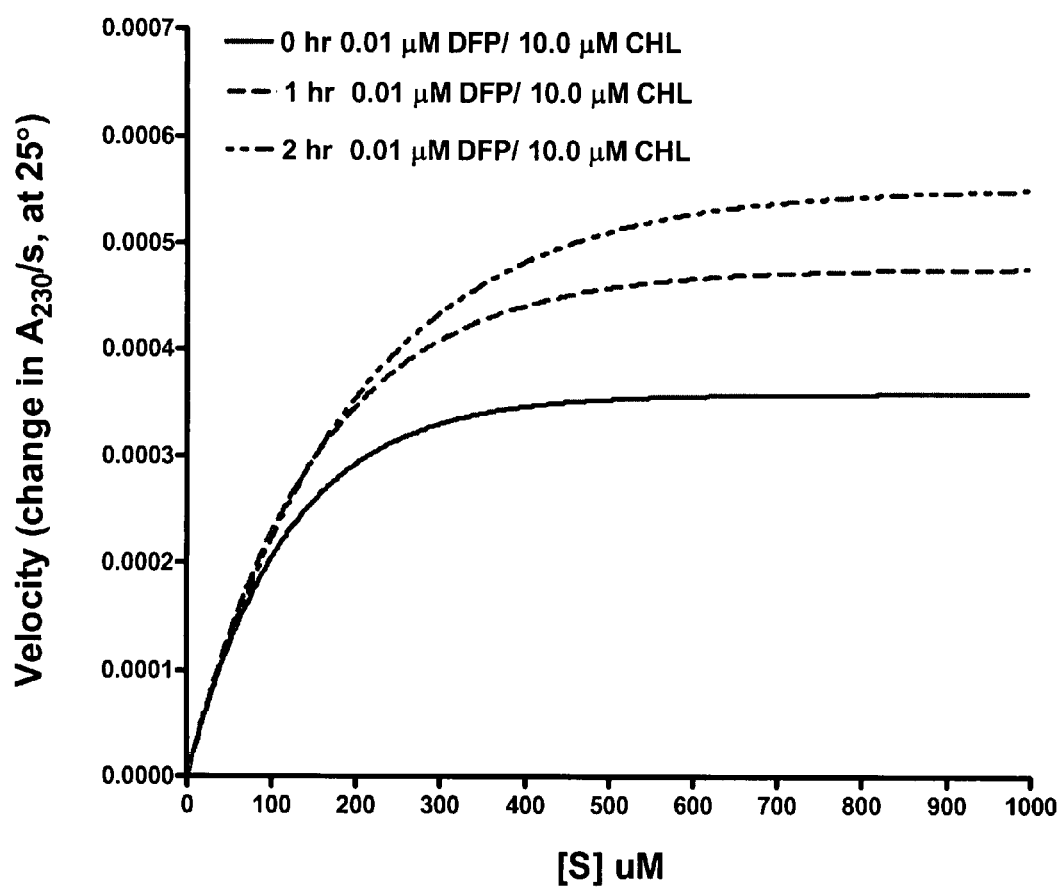
FIG. 5 is a graph of reaction velocity for the conversion of acetylcholine by acetylcholinesterase (measured as the change in absorbance at 230 nm per second) versus the concentration of acetylcholine (a Michaelis-Menten plot), where reaction velocities were measured in the presence of 0.01 µM DFP and 10 µM CHL that had been incubated for various times before addition to the enzyme solution.

The concentration of purified human recombinant acetylcholinesterase in a phosphate buffer was set at 0.02 µM. Three separate phosphate buffered solutions of DFP and CHL were prepared. Each DFP/CHL solution was either added to the solution of acetylcholinesterase immediately or allowed to incubate for one or two hours before being added to the solution. Addition of the DFP/CHL solutions to the enzyme resulted in final concentrations of 0.01 µM DFP and 10 µM CHL. After addition of the DFP/CHL solutions, increasing amounts of acetylcholine were added and the change in the absorbance of the solution at 230 nm was monitored as a function of time. The maximum substrate (acetylcholine) turnover rate was found to depend on the length of time that the DFP/CHL solution was incubated. As the DFP and CHL were incubated for longer periods of time, the activity of acetylcholinesterase increased. See FIG. 5.

EXAMPLE 5

This example provides experimental data demonstrating substantially pure chlorophyll produced according to disclosed embodiments significantly increased efficacy.

Chlorophyll was purified from spinach as described in Example 1, to a level of 97% purity by HPLC analysis. For comparison, a sample of impure material was obtained without using counter current chromatography, and assessed as 90% pure by HPLC, a level of purity typical of commercially available chlorophyll a or b. These two preparations were separately incorporated into the standard test diet at 2000 ppm, and fed for one month to replicate groups of 100 rainbow trout, along with a known carcinogenic dose of dibenzo [a,l]pyrene. The amount of total chlorophyll included in the two diets was identical, so that efficacy could be related on a molar basis. Additional control groups also were studied; one with 4000 ppm of 90% pure chlorophyll in the standard diet without dibenzo[a,l]pyrene and one with fully oxidized chlorophyll at 2000 ppm in the standard diet with dibenzo[a,l] pyrene. After one month treatment all groups were returned to standard diet, reared an additional 10 months for tumor development, and tumors assessed by published methods (e.g. Reddy et al., 1999).

TABLE 3

Effect of Substantially Pure Chlorophyll on Tumors in Trout after Exposure to 112 ppm dibenzo[a, l]pyrene

| Chlorophyll in diet (ppm) | Dibenzo[a, l]pyrene (ppm) | Liver Tumor Incidence (%) | Stomach Tumor Incidence (%) |
|---|---|---|---|
| 0 | 0 | 0 | 0 |
| 4000 (90% pure) | 0 | 0 | 1.6 ± 0.6 |
| 0 | 112 | 57.0 ± 2.1 | 21.1 ± 1.7 |
| 2000 (oxidized) | 112 | 47.0 ± 4.3 | 19.6 ± 1.0 |
| 2000 (90% pure) | 112 | 30.8 ± 3.1 | 14.3 ± 1.0 |
| 2000 (97% pure) | 112 | 14.2 ± 2.5 | 6.6 ± 1.2 |

As seen in Table 3, carcinogen alone produced a strong tumor response in stomach (21% incidence) and liver (57% incidence). The 90% pure chlorophyll reduced these incidences (by one third in stomach; nearly one half in liver), whereas the highly purified chlorophyll provided much greater tumor reduction (over two thirds in stomach, three fourths in liver), despite being fed at the same molar dose of chlorophylls a and b as the impure material. In the same study oxidized chlorophylls were tested, as may be encountered in improperly purified or stored chlorophyll. This material was nearly devoid of protective activity. These results in sum demonstrate that the disclosed embodiments of the invention produce highly pure chlorophyll or derivatives thereof and that the highly pure chlorophyll or derivatives thereof have substantially improved chemoprotective activity in our standard cancer bioassay, and the necessity to produce stabilized formulations in order to retain biologic activity.

EXAMPLE 6

This example concerns administering materials produced according to Examples 1 and 2 to subjects. Test solutions were prepared as follows.
Preparation of Test Solutions Concentrated stocks (>1 mg/ml) of $AFB_1$ were first prepared in dichloromethane and diluted to working concentrations in ethanol prior to dilution in the tricaprylin gavage. Final ethanol concentration in gavage solutions was less than 1% (v/v). Concentrated solutions of CHL were prepared in water and diluted to the administered concentration in tricaprylin gavage vehicle. Chl is virtually insoluble in water, thus Chl solutions were prepared in petroleum ether, diluted to a working stock in ethanol, and diluted to the administered concentration in tricaprylin gavage vehicle. Gavage solutions were monophasic with the exception of the $AFB_1$-CHL co-gavage in which the non-chlorin salt fraction was insoluble.
Animals and Diets For the adduct study male F344 rats, 75-100 g (Simonsen Laboratories, Inc., Gilroy, Calif.), were housed individually in metabolism cages, for easy collection of separate urines and feces, and maintained at 22° C. on a 12 hr light/dark cycle. For the liver and colon foci study male P344 rats, 75-100 g, were housed two per cage in standard barrier. Rats were acclimated to AIN-93G diet (Dyets Inc., Bethlehem, Pa.) without ethoxyquin antioxidant and fed ad libititum for 1 week prior to the period of carcinogen exposure.
Adduct Study After 1 week on the acclimation diet the rats were randomly assigned to one of three treatment groups. The experimental treatments are summarized in Table I. Group 1 (N=7) received by gavage 250 µg of [$^3$H]-$AFB_1$ (260 µCi/µmol) per kg of body wt (0.208 µCi/g body wt) in 3 µl of tricaprylin per gram of body weight. Group 2 (N=7) received the same

[³H]-AFB₁ dose mixed with 250 mg CHL. (as Cu chlorins) per kg body weight. Group 3 (N=7) received the same [[³H]-AFB₁ dose mixed with 300 mg Chl per kg body weight. The amount of Chl administered was equimolar with the amount of CHL administered and, based on in vitro binding measurements, was calculated to complex at least 90% of the AFB₁ in the gavage solutions at 25° C. All 7 rats per group were gavaged on days 0, 1 and 2. Two hrs after the day 2 gavage, 4 rats from each group were euthanized for tissue collection. The remaining 3 rats per group were gavaged on days 3 and 4, and 2 hrs after the day 4 gavage the remaining rats were euthanized for tissue collection. Rats were weighed daily throughout the experiment.

Isolation of DNA and Analysis of Hepatic Alatoxin-DNA Adducts

Rats were euthanized with $CO_2$ on the indicated 2 hours after gavage dosing. The liver was excised, cut into pieces of approximately 100 mg which were divided equally between two 50 ml centrifuge tubes, and immediately frozen in liquid $N_2$ for later use. Approximately 1.2 grams of frozen liver pieces were placed in 20 volumes of DNAzol reagent (Molecular Research Center, Inc., Cincinnati, Ohio) and homogenized with a few pulses of an Ultra-Turrax T8 homogenizer (IKA Works, Wilmington, N.C.). DNA extraction using DNAzol was according to the manufacturer's protocol, and quantification of I)NA yield was done with PicoGreen reagent (Molecular Probes, Eugene, Oreg.). A known mass of purified DNA (average about 1 mg) from each liver was directly counted in a Beckman 7500 liquid scintillation counter as a measure of total aflatoxin equivalents per milligram of DNA (signal:noise ratio>100 for all samples).

Quantification of Aflatoxin Serum Albumin Adducts

Blood (approx. 1 ml) was collected from each rat on gavage day 2 or 4 at necropsy. The blood was centrifuged at 300 g for 5 minutes and the resultant serum was removed and stored at −80° C. until analysis. The serum albumin was purified by the method of Chapot and Wild and quantified using Bradford dye-reagent and albumin standards (Bio-Rad Laboratories, Hercules, Calif.). The samples were prepared for liquid scintillation counting by mixing 0.5 ml of purified albumin sample (1-2 mg albumin) with 1 ml Soluene 350 tissue solubilizer (Perkin Elmer) in a glass scintillation vial and heating the mixture at 55° C. for 1 hour. After cooling, 10 ml of Hionic Fluor LSC fluid (Perkin Elmer) was added to the solubilized sampled and total $AFB_1$ equivalents were determined radiometrically in a Beckman 7500 liquid scintillation counter (signal noise ratio>100 for all samples).

Urinary AFB-$N_7$-Guanine and Fecal AFB Equivalents

Twenty-four hour urine samples were normalized using a spectrophotometric creatinine kit (TECO Diagnostics, Anaheim, Calif.). Urine aflatoxin metabolites were recovered using an aflatoxin-specific preparative monoclonal antibody immunoaffinity column. Metabolites were identified and quantified by electrospray-mass spectrometry. Twenty-four hour fecal samples, approximately 1 g. were weighed, homogenized in 10 volumes of water, and 0.5 ml aliquots were decolorized overnight at room temperature with 30% hydrogen peroxide. A 0.1 ml aliquot of each sample (2 mg feces) was mixed with 10 mls of Bionic Fluor LSC fluid and counted in a Beckman 7500 liquid scintillation counter (signal:noise ratio>100 for all samples).

$AFB_1$ Interactions with CHL and Chl In Vitro

Formation of a non-covalent complex between $AFB_1$ and CHL or highly purified Chl was assessed by quenching of $AFB_1$ fluorescence as described previously in detail for quenching of $AFB_2$ ($AFB_1$ structural derivative) fluorescence by CHL. Dissociation constant ($K_a$) determinations could not be carried out in the tricaprylin gavage solvent due to the strong fluorescence of that compound. We instead used a close approximation to tricaprylin, triethylene glycol (pH 8.0), an amphipathic solvent that provided appropriate linearity of $AFB_1$ fluorescence and sensitivity for monitoring quenching. Triethylene glycol was not used for gavage cosolvent due to its dehydrating effect on rats. The initial concentration of $AFB_1$ (substrate) was 10 µM in a 3 ml stirred quartz cuvette. CHL or Chl was added in 1.33 µM increments up to 31.92 µM CHL or Chl, with negligible increase in assay volume from ligand additions. Fluorescence was monitored at 428±8 nm with excitation at 368±8 nm, and was recorded 2 minutes after each ligand addition on an SLM 8000 photon counting spectrofluorometer (SLM AMINCO, Urbana, Ill.). The fluorescence quenching data were iteratively fitted to 1:1 and 2:1 AFB1:CHL or Chl models of binding stoichiometry.

Phase 2 Enzyme Responses

Two additional treatment groups indicated in Table 1 (N=2 rats each) were gavaged concurrently with the rats in the adduct study and were used to measure phase 2 responses due solely to CHL or Chl exposure. These groups gavaged on days 0-2 only, with 250 mg/kg CHL (as Cu chlorins) in tricaprylin, or with 300 mg/kg Chl in tricaprylin. Approximately 0.5 g of frozen rat liver from each rat in the adduct study was homogenized in 9 volumes of 3 mM Tris-HCL, pH 7.4 with 0.25 M sucrose and 1 mM EGTA, then centrifuged at 100,000 g to yield microsome-free cytosol. The cyctosolic protein concentration of each sample was determined using the Bradford dye-reagent with albumin standards. Cyctosols were stored as 200 µl aliquots at ~80° C. for enzyme assays. The Prochaska bioassay was used to measure the activity of NAD(P)H: quinone oxidoreductase (NQO) using dilute cytosol in triplicate assays. Afterward, the rate of each reaction was normalized to the sample protein content as determined by crystal violet staining. The activity of GST was similarly assayed, but at 340 nm at 25° C., with 1-chloro-2,4-dinitrobenzene (CDNB) as the substrate. One ml of 0.1 M potassium phosphate, pH 6.6, reaction buffer contained 50 µl mM GSH, 50 µl 20 mM CDNB (ethanolic stock), and dilute cytosol. The reaction rate was measured at 1 minute intervals for 5 minutes on a Beckman Coulter DU 800 spectrophotometer.

Late Pathophysiological Marker Study

Forty-two male F344 rats (mean weight 140 g) were arranged into 6 treatment groups. The experimental treatments are summarized in Table I. Groups 1-3 (N=10 rats each) were experimental groups. and groups 4-6 (N 5, 4 and 3 rats each, respectively) were controls. Group I received 250 µg/kg body weight $AFB_1$ in tricaprylin. Group 2 received 250 µg/kg $AFB_1$ plus 250 mg/kg body weight CHL (as Cu-chlorin content) in tricaprylin. Group 3 received 250 µg/kg $AFB_1$ plus 250 mg/kg Chl in tricaprylin. Group 4 received tricaprylin only and group 5 and group 6 received 250 mg/kg CHL and Chl, respectively. All treatments were administered by gavage (3 µl/g body weight) 5 times per week for 2 weeks. One rat in group 1 died at week 5 and thus, group I ended with N=9 rats. After 18 weeks, all rats were killed by $CO_2$ asphyxiation, the livers removed and weighed. For GST-P quantification, two 3 mm sections were cut by hand from the median lobe of the liver and fixed in acetone. Sections were processed for histology using the AMeX fixation and processing procedure. Slides were stained for expression of GST-P and examined by light microscopy. The volume percent of liver occupied by GST-P positive foci is considered the least biased and most predictive estimate of eventual tumor burden; therefore, this was the primary endpoint evaluated. All samples were coded so that the individual analyzing them was blinded to the treatment group. Aberrant crypt foci (ACF) quantification was done according to Orner et al. Briefly, colons were removed, washed with cold phosphate buffered saline, fixed mucosal side up in 10% phosphate buffered formalin, stained with 0.2% methylene blue, and AFC scored as previously described. The samples also were a coded for blinded analysis.

Statistical Analyses

Data for the DNA adducts, serum albumin adducts, fecal $AFB_1$ equivalents and phase 2 enzyme responses were analyzed by comparing treatment means to the control group mean by a standard ANOVA model (homogeneous variance and Dunnett's adjustment to minimize type 1 errors). For the urinary data, heterogeneous variance in statistical comparisons of treatment effects necessitated natural log (ln) transformation of the raw data. The variance of the ln-transformed data was first tested for homogeneity using ANOVA of the squared deviations from the treatment means for each metabolite. This comparison indicated that variance among the treatments within in each metabolite category was homogenous (P> F value), and that treatment means of the ln transformed data could be compared by t-test. Dunnett's adjustment for multiple comparisons was applied to the t-tests to minimize type I errors. All calculations were performed using SAS version 9.1 (SAS Institute, Inc.). Statistical analysis of the GST-P positive foci data was by ANOVA, followed by a Bonferroni multiple comparison test to determine differences between individual groups. Statistical analysis of the ACE data was by ANOVA and post hoc Fisher's PLSD test.

Results

Chl and CHL Effects on $AFB_1$ DNA Adduction In Vivo

Figure 10:
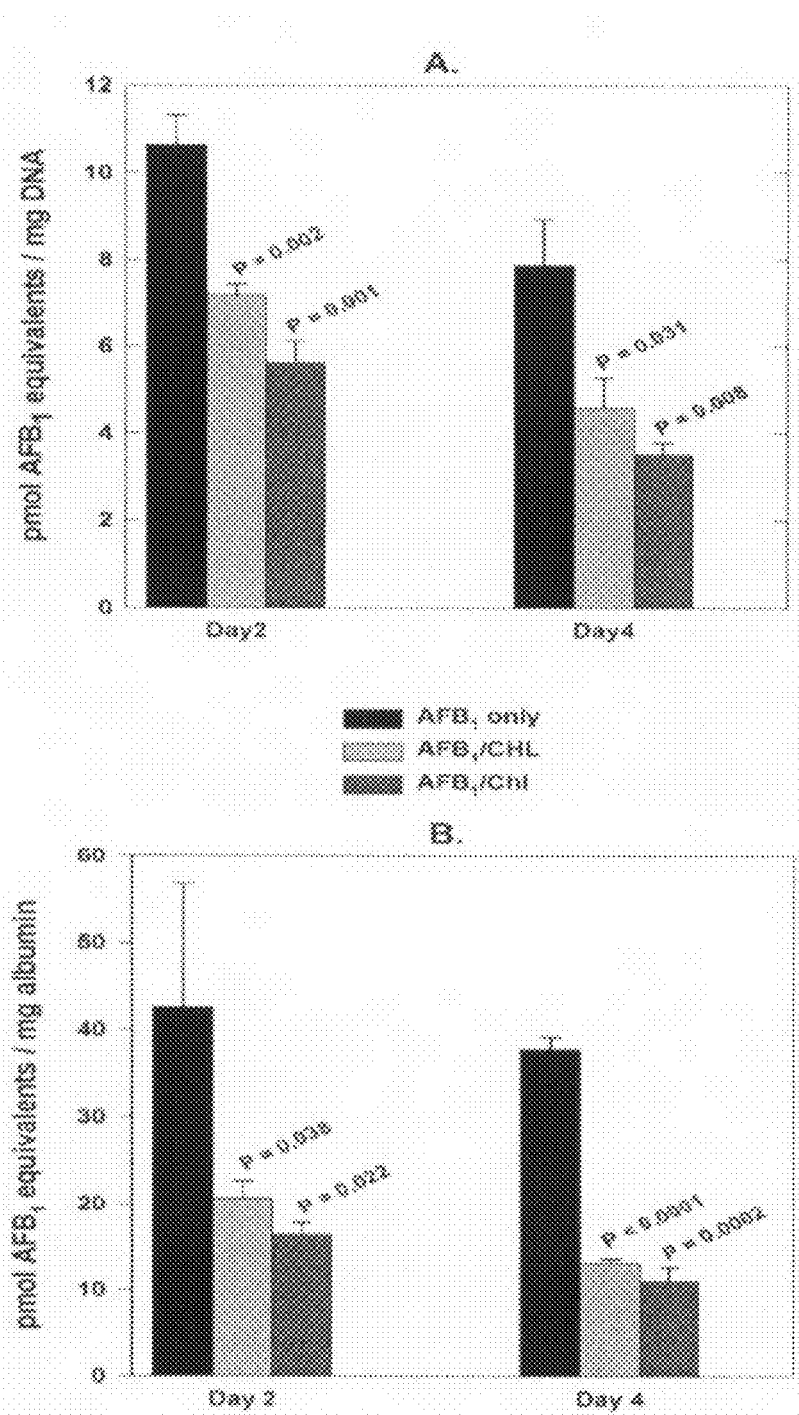
FIG. 10A is a graph of pmol $AFB_1$/mg DNA versus time for compositions comprising $AFB_1$, $AFB_1$/CHL and $AFB_1$/Chl.
FIG. 10B is a graph of pmol $AFB_1$/mg albumin versus time for compositions comprising $AFB_1$, $AFB_1$/CHL and $AFB_1$/Chl, illustrating the effect of chlorophyll on AFB1-induced hepatic DNA adduction and serum albumin adduction, where hepatic DNA adduction was measured from samples collected 2 hours after the third gavage (Day 2) and the fifth gavage, and serum albumin adduction was measured from blood samples. Values stated are the mean ±SE for N=4 rats per group on day 2 and N=3 rats per group on day 4. The probability value (P) for treatment difference from the AFB1 or vehicle control group is indicated above each treatment bar. $P<0.05$ was considered significantly different.

The effects of CHL and Chl on hepatic $AFB_1$-DNA adduction in rats that received 250 μg [3H]-$AFB_1$/kg by gavage for 5 days are shown in FIG. 10 (panel A). Liver samples were taken on two separate days at 2 hours post-dosing, the time of maximal AFB-$N^7$-guanine levels in the rat liver. The overall DNA adduction level, measured as [$^3$H]-$AFB_1$ equivalents, among the three treatments was slightly higher on day 2 than day 4. This is consistent with previous studies in which the maximum levels of carcinogen binding to hepatic DNA are observed following the first few doses of $AFB_1$, and decline thereafter, despite continued exposure. Co-gavage with 250 mg/kg CHL or the molar equivalent dose of 300 mg/kg Chl reduced hepatic DNA adduction by 33% (P 0.003) and 47% (P 0.001), respectively relative to the control group by day 2. At 2 hours after the day 4 gavage, the control group adduct level had declined somewhat from day 2, but protection by CHL and Chl remained substantial, with adducts decreased by 42% (P 0.031) and 55% (P-0.008) respectively, relative to the control group.

Chl and CHL Effects on $AFB_1$ Serum Albumin Adduction

Serum albumin is the major blood protein to be adducted following metabolic epoxidation of Chl and CHL effects on $AFB_1$. The levels of aflatoxin-serum albumin adduction were measured radiometrically and the impact of CHL and Chl on albumin binding is shown in FIG. 10 (panel B). The temporal pattern of albumin-adduct formation and the degree of chemoprotection is similar to that seen in the DNA. Day 2 showed an overall higher level of adduction and both the CHL and Chl co-treatments significantly reduced adducts by 52% (P 0038) and 62% (P 0.022), respectively relative to the positive control group. On day 4, as we observed for DNA adduction, the degree of protection by CHL and Chl remained significant, with 65% (P<0.001) and 71% (P<0.001) respective reductions in albumin adducts. Also, as seen with DNA adducts CHL and Chl protection on day 4 appeared slightly greater than on day 2, though not significantly so.

Chl and CHL Effects on Urinary and Fecal Elimination of Aflatoxin Metabolites

Previous studies have shown that, in mammals, the major AFB-$N^7$-guanine adduct is rapidly excised and excreted via the urine, and that CHL-impeded absorption of $AFB_1$ results in lower levels of excised DNA adducts in the urine, and correspondingly higher $AFB_1$ equivalents in the feces. Table II shows the mean levels of the AFB-$N^7$-guanine adduct and two major less toxic aflatoxin metabolites, $AFM_1$ and $AFP_1$, in 24 hour urine samples taken on day 4 (N=3 rats/treatment). Statistical comparisons were made on natural log transformed data and reported on the original ($e^x$) scale. The level of the AFB-N7-guanine adduct excreted in the urine was significantly reduced by 90% (P=0.0047) and 92% (P=0.0029) by co-gavage with CHL and Chl, respectively compared to the control group. $AFM_1$ in the urine was significantly reduced by 63% (P 0.0173) and 81% (P=0.0016) by CHL and Chl, respectively. $AFP_1$ excretion to the urine was also significantly reduced by 90% (P=0.0003) and 92% (P=0.0002) by CHL and Chl, respectively. The relative amounts of protection by CHL and Chl against the urinary $AFB_1$-DNA repair product and $AFP_1$ metabolite were identical. CHL and Chl appeared slightly less effective in reducing the level of AFM1 in urine, but the basis for this unclear.

Figure 11:
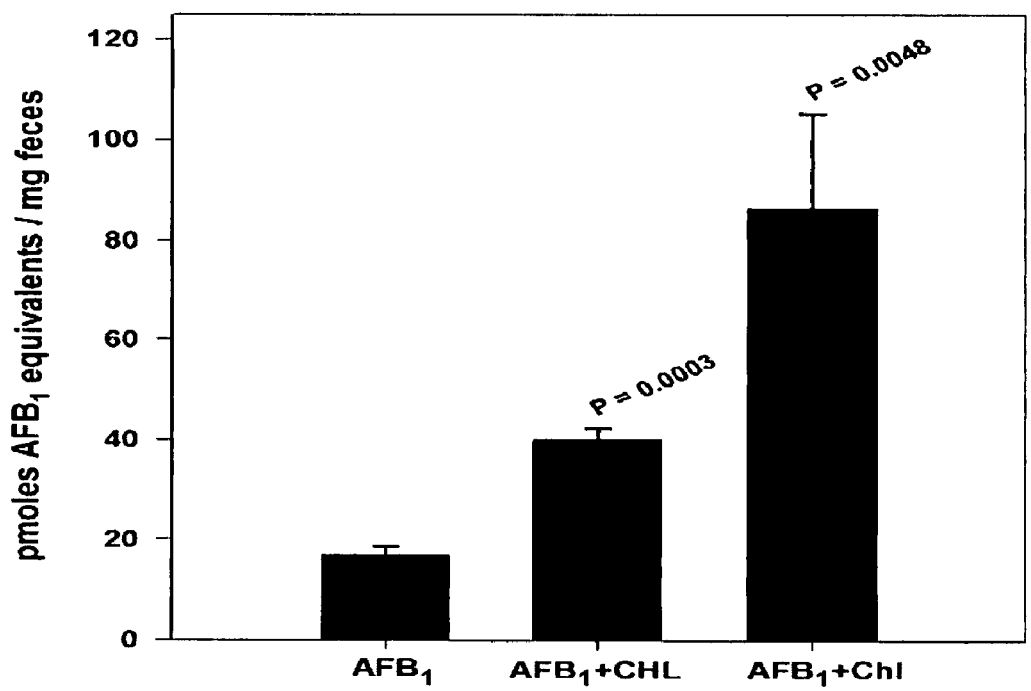
FIG. 11 is a graph of pmol $AFB_1$ equivalents/mg feces for compositions comprising $AFB_1$, $AFB_1$/CHL and $AFB_1$/Chl, illustrating the effect of chlorophyll on fecal elimination of AFB1 equivalents, where 24 hour fecal samples were collected 2 hours after the day 4 gavage, values are the mean ±SE for N=3 rats per group, and the probability value (P) for treatment difference from the AFB1 control group is indicated above each treatment bar, with $P<0.05$ considered significantly different.

Conversely, the day 4, 24 hour feces from the CHL and Chl co-gavaged rats contained 137% (P=0.0003) and 412% (P=0.0048) more $AFB_1$ equivalents, respectively, than did feces of the control group (FIG. 11). The fecal elimination of $AFB_1$ equivalents in the Chl co-treated rats was two fold greater (P 0.0212) than the elimination by CHL co-treated rats, a larger difference between CHl and Chl effects than seen with any other parameter except urinary $AFM_1$ excretion.

CHL and Chl Interactions with $AFB_1$ In Vitro

CHL forms a strong non-covalent 1:1 complex with $AFB_1$ and $AFB_2$ (8, 9 position saturated derivative) in vitro ($K_d$=1.4 μM and 1.92 μM, respectively). Importantly, those studies demonstrated that inclusion of CHL at sufficient concentration to achieve 99% calculated complexation of aflatoxin strongly and significantly reduced hepatic DNA adduction, and aflatoxin uptake and biodistribution. The present example compares the ability of natural CHL and Chl to complex with $AFB_1$ under similar co-solvent conditions, as a possible mechanism of Chl chemoprotection. The tricaprylin co-solvent used for gavage was strongly fluorescent in the emission range used and thus, was inappropriate for quench measurement. Triethylene glycol (TEG) provided a suitable approximation to tricaprylin. Titration of $AFB_1$ in TEG with CHL or Chl in 1.33 p.M increments resulted in quenching of the $AFB_1$ fluorescence spectrum between 380 and 550 nm (FIG. 13A, CHL data not shown).

Figure 13:
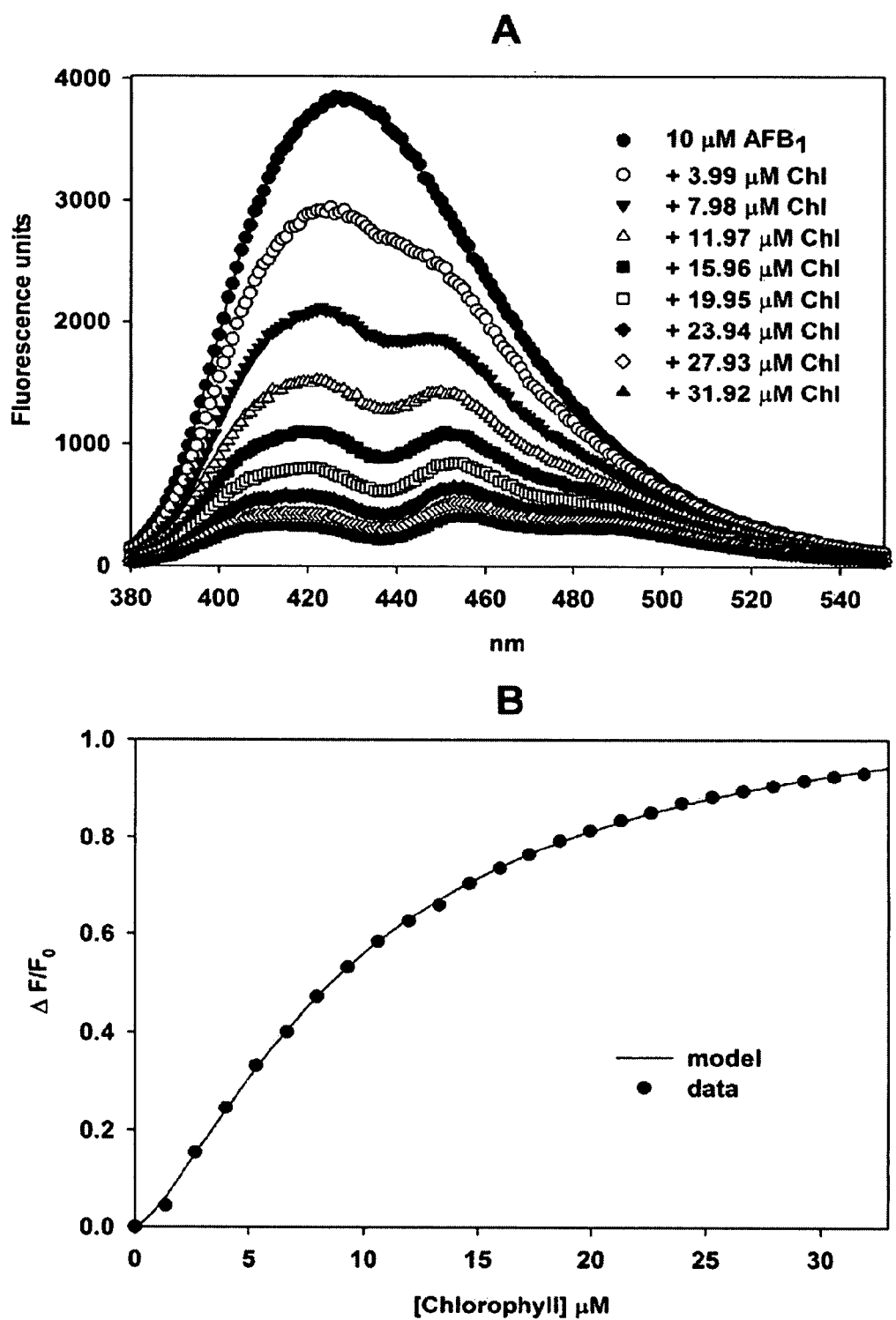
FIG. 13A is a graph of fluorescence intensity versus wavelength for spectrofluorometric titration of AFB1 illustrating the effect of Chl on the AFB1 emission spectrum from 380 to 550 (±8) nm (excitation 368±8 nm) with AFB1 (substrate) concentration at 10 µM. Chl (ligand) was added in 1.33 µM increments up to 31.92 µM (some titrations omitted from the figure for clarity) and the spectrum was recorded 2 minutes after each addition.
FIG. 13B is a graph of $\Delta F/F_0$ versus chlorophyll concentration (µM) illustrating quantification of Chl quenching of AFB1 fluorescence at 428±8 nm recorded from the above spectra. Data were normalized by converting fluorescence units to $\Delta F/F0$ and the data was fitted to a 1:1 Chl:AFB1 complexation model.

To quantify CHL and Chl quenching of $AFB_1$ fluorescence, the fractional fluorescence change ($\Delta F/F_0$) at 428 nm emission with each titration was plotted and a model assuming a 1:1 ratio of CHL or Chl to $AFB_1$ binding and zero fluorescence yield of hound $AFB_1$ was fitted (FIG. 13B, CHL data not shown). This model provided an excellent fit to the data for CHL and Chl binding ($r^2$=0.9999) and yielded a $K_d$=3.05±0.04 μM for Chl, and a $K_d$=1.22±0.05 μM for Chl. Modeling assuming a 2:1 $AFB_1$:CHL or Chl binding stoichiometry yielded a poor fit to the data (not shown). In sum, with conditions approximating the gavage solvent, the in vitro binding of Chl to $AFB_1$ was approximately 2.5 times stronger than the binding of CHL to $AFB_1$.

Chl and CHL Effects on Hepatic Phase 2 Enzyme Responses

Induction of phase 2 enzymes is an important and, in some cases, a sufficient detoxification response to block chemical carcinogenesis. Table III shows the activity levels of GST and NQO on gavage days 2 and 4 in each treatment. Neither CHL nor Chl co-treatment significantly increased the basal activity of either enzyme above that seen in the $AFB_1$ control livers (F>0.05). The standard ANOVA model indicated evidence of decreased GST activity relative to $AFB_1$ on day 4 in the (CHL (P=0.037) and Chl (P=0.0043) co-treatments. Treatment with CHL or Chl alone (measured from day 2 only) did not induce GST or NQO. In sum, these data provide no evidence for induction of hepatic phase II enzymes in vivo following CHL or Chl treatment.

Chl and Chl Effects on $AFB_1$ Preneoplastic Lesions in the Rat Liver and Colon

Rats administered $AFB_1$ showed an 11% slower growth rate (P<0.05), regardless of co-treatment, for the first 4 weeks of the treatment compared to the non-$AFB_1$ treated rats (data not shown). By the fifth week of the 18 week study all rats had attained the same growth rate. Treatment with vehicle +CHL or Chl had no effect on growth relative to treatment with vehicle only.

Figure 12:
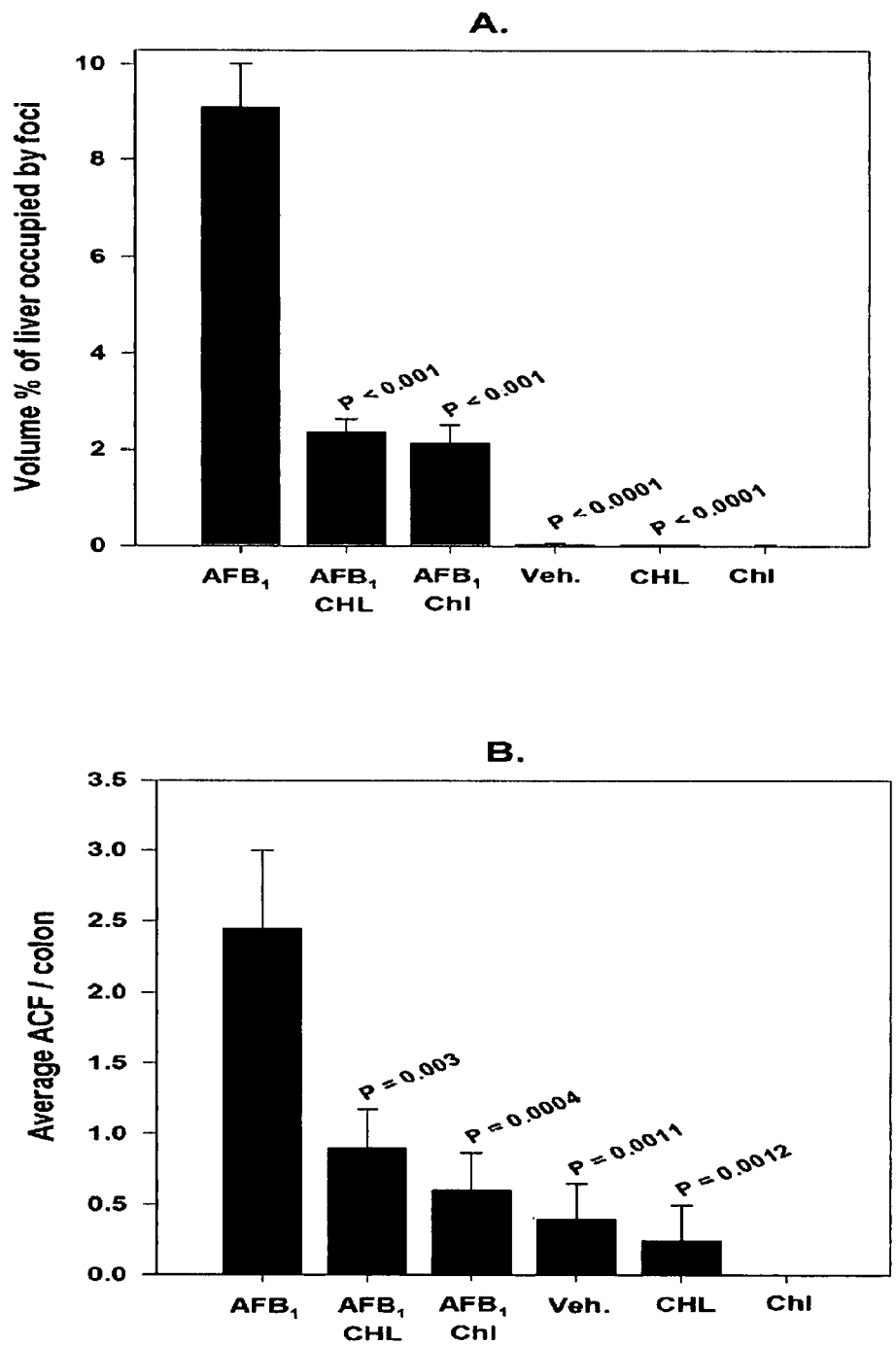
FIG. 12A is a graph of volume percent of liver occupied by foci for $AFB_1$, $AFB_1$/CHL, $AFB_1$/Chl, vehicle, CHL and CHL with Chl illustrating effects of chlorophyllin and chlorophyll on the hepatic burden of AFB1-induced GST-P positive foci and the colonic burden of aberrant crypt foci. Rats were gavaged 5 times per week for 2 weeks as described in Materials and methods, killed 18 weeks after the last gavage, and the livers and colons were processed as described. Samples from both organs were coded and scored blind. (A) volume % of the liver occupied by GST-P foci.
FIG. 12B is a graph of average ACF/colon for $AFB_1$, $AFB_1$/CHL, $AFB_1$/Chl, vehicle, CHL and Chl illustrating aberrant crypt foci per colon. Values in A and B are the mean ±SE for N=9, 10 and 10 rats in experimental groups 1-3, respectively. The vehicle, CHL and Chl negative control groups had N=5, 4 and 3 rats, respectively. The probability value (P) for treatment difference from the AFB1 control group is indicated above each treatment bar. $P<0.05$ was considered significantly different.

The volume percent of liver occupied by GST-P positive foci is considered the least biased and most analogous focal predictor of final tumor burden and, therefore, was the primary endpoint evaluated. Chl and CHL equally and significantly (P<0.001) reduced the volume % of liver occupied by GST-P positive foci (FIG. 12A). GST-P positive foci were seldom observed in vehicle and Chl or CHL control rats. The focal density in the liver (foci/cm$^3$) was the same between the three aflatoxin treated groups. Chl co-treatment significantly (P<0.01) reduced mean focal diameter compared to $AFB_1$ exposure alone, and the effect of CHL on this parameter approached significance (P=0.084; data not shown). The effect of CHL and Chl co-treatments on colon aberrant crypt foci (ACF) is shown in FIG. 12B. $AFB_1$ treatment resulted in 2.4±0.6 (mean ±SE) ACF per colon, but co-treatment with CHL or Chl significantly reduced this ratio to 0.9±0.3 (P=0.0026) and 0.6±0.3 (P=0.0004), respectively. The number of crypts per ACF (focus size) did not differ significantly among the treatments.

The above examples demonstrate substantial protection by natural chlorophyll against $AFB_1$ carcinogenesis in subjects as exemplified by carcinogenic protection in the rat liver and colon. Hepatic DNA-adduct and serum albumin adduct burdens were dramatically reduced in Chl co-exposed rats compared to controls. The hepatic and colonic burdens of presumptive pre-neoplastic foci also were dramatically reduced by Chl co-exposure.

Mechanistic studies on rodents and trout indicate that the degree of attenuation of $AFB_1$-DNA adducts by dietary chemopreventive agents is closely correlated with reduced incidence of pre-neoplastic lesions and reduced tumor incidence. A previous study in rats showed that gavage with 100 mg of CHL immediately followed by gavage of 10 μg of [3H]-$AFB_1$ resulted in a 45% decrease in the level of hepatic DNA adducts. This level of protection was mirrored by commensurate decreases in serum albumin adducts and urinary excretion of aflatoxin equivalents. The examples provided in the present application extend those findings by demonstrating that CHL cotreatment also protects against $AFB_1$-induced pre-neoplastic lesions in liver as well as colon.

The precise mechanism of Chl protection during co-exposure with AFB1 is not currently known. It appears that Chl does not protect by eliciting phase 2 enzyme detoxication of $AFB_1$ when co-administered with the carcinogen. Analysis of hepatic NQO and GST activity levels in rats co-exposed to $AFB_1$ and CHL or Chl indicated no increase in these phase 2 activities relative to the $AFB_1$ exposed livers. This result was unexpected in light of the recent report that CHL, Chl and related tetrapyrroles induced NQO activity in cultured murine hepatoma cells. In that study induction was significant, though Chl was not a potent inducer with a concentration required to double NQO activity (CD) of 250 μM. Chlorophyllin, however, was nearly 10 times as potent an inducer of NQO (CD=30 μM). The relatively poor inducing potency for Chl in vitro may reflect poor uptake into these cells. Data on the metabolism of Chl in the whole animal gut as well as uptake of Chl or its oxidation products from the gut are very limited, but for decades the central assumption has been that Chl uptake in vivo is not significant. Poor bioavailability, however, is an unlikely explanation for the finding that CHL co-exposure did not induce NQO. The bioavailability of CHL components, especially chlorin e4 ethyl ester, is well established [49], and the ethyl ester component (CD=20 μM) is 50 times more potent an NQO inducer in vitro than Chl [22]. Our NQO results with CHL co-exposure may reflect the inherent gap between cell culture and whole animal studies. Alternatively, differences in the dose and timing of CHL administration may account for different phase 2 induction. Dingley et al. showed that rats given dietary CHL (10 g/kg diet) for two weeks prior to a single low dose co-gavage of two heterocyclic amine carcinogens, had a 1.6 fold increase in NQO activity relative to control animals 24 hours after the carcinogen dose, but no change in GST activity. There are, however, substantial protocol differences in that study (a 40-fold higher concentration of CHL in the diet, administration of CHL for 2 weeks prior to the carcinogen) that might account for the difference in NQO induction. A whole animal study comparing multiple doses of CHL and Chl, and pre versus co-initiation protocols may help shed light on the relative importance of phase 2 metabolism in CHL and Chl chemoprevention.

Both CHL and Chl given co-initiation (during carcinogen exposure) were quite effective in reducing putative pre-neoplastic foci in the colon, and the liver. Consumption of chemoprotectants by humans is likely to involve these agents acting on previous as well as concurrent initiation events. Thus, the post-initiation effects of CHL and Chl are important. A companion study in the rainbow trout model included examination of the co-versus post-initiation effect of 2000 ppm dietary CHL on dietary dibenzo[a,l]pyrene (DBP) initiated tumors in multiple organs. Post-initiation CHL for 9 months significantly promoted swimbladder tumor incidence from 10 to 38%, and promotion approached significance in the stomach. Co-initiation CHL had no effect in the swimbladder, but significantly inhibited tumor incidence by 30% in the liver and stomach. In the rat, post-initiation treatment with 0.1% CHL in the drinking water (approximately half the daily gavage dose in our study) for 20 weeks reportedly increased the incidence of DMH-induced colon tumors from 10 to 47%. In another study, post-initiation treatment of rats with 0.001, 0.01 or 0.1% CHL in the drinking water for weeks significantly increased the multiplicity of DMH-initiated colon tumors only at the 0.001% CHL dose. In that same study, the same CHL regimen inhibited in a dose-related manner dietary IQ-initiated liver tumors, but had no effect on IQ-initiated colon tumors. A follow-up study to reported that 0.001% CHL in the drinking water for 16 weeks after IQ gavage significantly increased IQ-induced ACF. Importantly, that study also included an experiment that showed post-initiation treatment with 0.08% dietary natural chlorophyll (approximately equivalent to 0.1% in the drinking water) inhibited azoxymethane- (a metabolite of DMH) and IQ-induced aberrant crypt foci. Collectively, the pattern of post-initiation effects of CHL and Chl appears to depend heavily on several factors including concentration and duration of post-initiation exposure, and the initiating carcinogen.

The present application provides evidence that Chl inhibits uptake of AFB1 from the rat stomach, and that it does so with equal or greater efficacy than CHL. In pharmacokinetic compartments outside the gastrointestinal (GI) tract such as the liver, serum and urine, the adduct burden was reduced over a 2-13 fold range by Chl coexposure, while in the feces of the same animals, roughly 5 fold more AFB1 equivalents were eliminated relative to the control animals. Thus, Chl co-exposure largely restricted AFB1 to the GI tract. Moreover, substantial protection by Chl against ACF development in the colon suggests that, in addition to restricting AFB1 to the GI tract, Chl treatment reduced AFB1 metabolism to toxic intermediates in the colon. One simple mechanism to explain inhibition of both uptake and colon metabolism of the carcinogen could be formation of a molecular complex between Chl and AFB1 in the gut. Tight CHL complexation with AFB1, some heterocyclic amine carcinogens, and dibenzo[a,l]pyrene (DBP) is easily demonstrated in vitro [13-15] using both fluorescence and absorbance spectrophotometry.

Examples presented in the present application establish that Chl is able to form an AFB1 complex of approximately 2.5 times greater stability in vitro. Interestingly, the chemoprotection afforded by Chl against AFB1-induced DNA damage, serum albumin adduction and multi-organ pre-neoplastic foci was slightly but consistently greater than the protection from an equimolar dose of CHL. The tighter Chl binding may explain the greater apparent in vivo protection by Chl. This possibility is supported by a recent report of Chl inhibiting the intestinal metabolism of heme to a cytotoxic metabolite. In this study, rats were fed diets supplemented with heme, heme plus Na- or Cu-chlorophyllin, or heme plus natural chlorophyll and assayed for several indicators of cytotoxicity in the fecal stream. Dietary Chl completely blocked heme-induced increases in colonocyte proliferation, cytotoxicity of the feces, and lipid peroxidation in the gut. Interestingly, CHL largely failed to inhibit the damaging effects of heme metabolism. Heme is a planar molecule, and like CHL and Chl, is a tetrapyrrole macrocycle that would reasonably be expected to complex via π-π orbital interactions. Because heme and CHL are negatively charged under physiological conditions, a repulsive force exists between heme and CHL preventing complex formation. Neutral Chl would not repel heme, and the higher octanol:water partition coefficients of Chl and heme might favor complex formation, especially within the lipid emulsion environment of the gut. To determine the relative importance of complex formation in protection by Chl, additional studies must establish a quantitative relationship between the amount of complexation over a range of values in the administered dose, and the resulting carcinogenic damage.

Two potential caveats are that examples provided by the present application concerned carcinogen and putative anticarcinogen exposure by gavage rather than by diet, and examined GST-P and AC foci as late (18 week) biomarker endpoints rather than tumors. Unfortunately, established protocols for high-incidence tumor induction by dietary $AFB_1$ in the rat require long-term exposure, and require substantial quantities of Chl, which can be provided, but only by scaling up substantially the disclosed Chl purification method. These potential caveats and limitations were circumvented by our companion study which used a well established short-term dietary treatment protocol to demonstrate profound Chl chemoprevention of histopathologically verified hepatic and intestinal tumors in the rainbow trout model. These two studies combined are the first to report protection against tumor development by oral or dietary Chl in any animal model, with protection observed in multiple organs and against two Prototypical classes of carcinogen.

Chl and CHL are potent chemoprotective agents against early biochemical and late pathophysiological biomarkers of $AFB_1$ carcinogenesis in the rat liver and colon. Fecal elimination and urinary metabolite studies provide supporting evidence that both agents protect by inhibiting carcinogen uptake from the gut, thus reducing the availability of $AFB_1$ to the target organ. Target organ protection in the form of CHL- or Chl-mediated hepatic induction of phase 2 detoxication enzymes was not a significant avenue of protection in the present study.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the accompanying claims. We therefore claim as our invention all that comes within the scope and spirit of these claims.

We claim:

1. A method for obtaining substantially pure chlorophyll from a suitable source comprising:
   providing a material containing chlorophylls; and
   obtaining substantially pure chlorophyll that is greater than 92% pure from the material by centrifugal partition chromatography.

2. The method according to claim 1 where the centrifugal partition chromatography is counter current chromatography.

3. The method according to claim 1 performed in dim light or no light conditions.

4. The method according to claim 1 where the source is algae, alfalfa or spinach.

5. The method according to claim 1 where the source is from the genus *Spirulina*.

6. The method according to claim 1 where the source is *Spirulina pacifica*.

7. The method according to claim 1 where the chlorophyll is greater than 95% pure.

8. The method according to claim 1 consisting essentially of liquid/solid extraction, liquid/liquid washing and centrifugal partition chromatography.

9. The method according to claim 1 further comprising forming a substantially pure chlorophyll derivative from the substantially pure chlorophyll.

10. The method according to claim 9 where the chlorophyll derivative has the structure depicted in Formula 1 or Formula 2, M is a metal ion with a charge of +2, $R_1$ is an aliphatic moiety, and $R_2$-$R_4$ independently are aliphatic

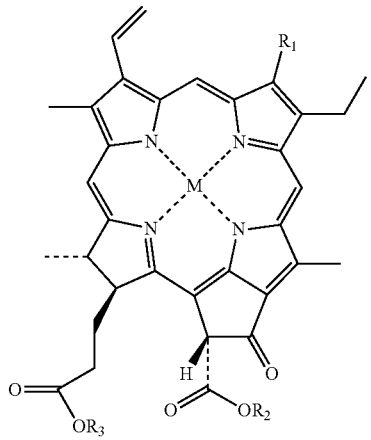

Formula 1

Formula 2

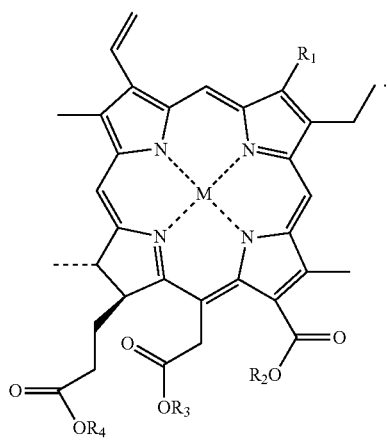

11. The method according to claim 10 where M is selected from beryllium, magnesium, calcium, strontium, barium, chromium, manganese, iron, cobalt, nickel, copper, zinc, molybdenum, technetium, ruthenium, rhodium, palladium, cadmium, tungsten, rhenium, osmium, iridium, platinum, and mercury.

12. The method according to claim 10 where $R_1$ is an alkyl group having fewer than 10 carbon atoms.

13. A method for obtaining substantially pure chlorophyll a from a suitable source comprising:
providing a material containing chlorophylls;
extracting the material with methanol/petroleum ether (3:1 v/v);
filtering the extracted material and discarding solid particles to provide filtered extracted material;
washing the filtered extracted material with saturated sodium chloride to produce a first organic layer and a first aqueous layer;
washing the first organic layer with saturated sodium chloride to produce a second organic layer and a second aqueous layer;
filtering the second organic layer and evaporating organic solvent to produce a residue;
dissolving the residue in acetone; and
obtaining substantially pure chlorophyll a that is greater than 92% pure from dissolved residue by centrifugal partition chromatography using heptane as a stationary phase and ethanol as a mobile phase.

\* \* \* \* \*